US012564612B2

(12) United States Patent
King et al.

(10) Patent No.: US 12,564,612 B2
(45) Date of Patent: *Mar. 3, 2026

(54) MICROBIAL STRAINS AND ANTIBIOTICS

(71) Applicant: MICROBIAL DISCOVERY GROUP, LLC, Franklin, WI (US)

(72) Inventors: Michael R. King, Oak Creek, WI (US); Sona Son, Cudahy, WI (US); Kyle Leistikow, Cudahy, WI (US)

(73) Assignee: MICROBIAL DISCOVERY GROUP, LLC, Franklin, IN (US)

( * ) Notice: Subject to any disclaimer, the term of this patent is extended or adjusted under 35 U.S.C. 154(b) by 365 days.

This patent is subject to a terminal disclaimer.

(21) Appl. No.: 18/022,400

(22) PCT Filed: Aug. 18, 2021

(86) PCT No.: PCT/US2021/046451
§ 371 (c)(1),
(2) Date: Feb. 21, 2023

(87) PCT Pub. No.: WO2022/040279
PCT Pub. Date: Feb. 24, 2022

(65) Prior Publication Data
US 2023/0321162 A1     Oct. 12, 2023

Related U.S. Application Data

(60) Provisional application No. 63/068,668, filed on Aug. 21, 2020.

(51) Int. Cl.
| | |
|---|---|
| *A61K 35/742* | (2015.01) |
| *A23K 10/18* | (2016.01) |
| *A23K 20/189* | (2016.01) |
| *A23K 20/195* | (2016.01) |
| *A23K 50/30* | (2016.01) |
| *A61K 31/395* | (2006.01) |
| *A61K 31/4025* | (2006.01) |
| *A61K 31/546* | (2006.01) |
| *A61K 31/65* | (2006.01) |
| *A61K 35/00* | (2006.01) |
| *A61K 45/06* | (2006.01) |
| *A61P 1/14* | (2006.01) |
| *A61P 31/04* | (2006.01) |

(52) U.S. Cl.
CPC ............ *A61K 35/742* (2013.01); *A23K 10/18* (2016.05); *A23K 20/189* (2016.05); *A23K 20/195* (2016.05); *A23K 50/30* (2016.05); *A61K 31/395* (2013.01); *A61K 31/4025* (2013.01); *A61K 31/546* (2013.01); *A61K 31/65* (2013.01); *A61K 45/06* (2013.01); *A61P 1/14* (2018.01); *A61P 31/04* (2018.01); *A61K 2035/115* (2013.01)

(58) Field of Classification Search
None
See application file for complete search history.

(56) References Cited

U.S. PATENT DOCUMENTS

| | | |
|---|---|---|
| 4,673,638 A | 6/1987 | Grosch et al. |
| 5,587,475 A | 12/1996 | Helquist et al. |
| 5,589,381 A | 12/1996 | Neyra et al. |
| 5,665,354 A | 9/1997 | Neyra et al. |
| 6,268,147 B1 | 7/2001 | Beattie et al. |
| 7,807,185 B2 | 10/2010 | Farmer |
| 8,025,874 B2 | 9/2011 | Bellot et al. |
| 8,540,981 B1 | 9/2013 | Wehnes et al. |
| 9,175,258 B2 | 11/2015 | Bywater-Ekegard et al. |
| 9,410,213 B2 | 8/2016 | Matheny et al. |
| 9,758,414 B2 | 9/2017 | Dash et al. |
| 9,844,573 B2 | 12/2017 | Nielsen et al. |
| 10,335,440 B2 | 7/2019 | King et al. |
| 10,961,275 B2 | 3/2021 | Bralkowski et al. |
| 2001/0027947 A1 | 10/2001 | Tsuchiya |
| 2004/0247582 A1 | 12/2004 | Binder et al. |
| 2005/0255092 A1 | 11/2005 | Rehberger et al. |
| 2005/0266468 A1 | 12/2005 | Bedzyk et al. |
| 2005/0271643 A1 | 12/2005 | Sorokulova |
| 2006/0188978 A1 | 8/2006 | Grant |
| 2007/0202088 A1 | 8/2007 | Baltzley et al. |
| 2008/0050774 A1 | 2/2008 | Berka et al. |
| 2008/0160067 A1* | 7/2008 | Boeckh ............... A61K 9/0056 424/441 |
| 2009/0238907 A1 | 9/2009 | Farmer |
| 2009/0280090 A1 | 11/2009 | Rehberger et al. |

(Continued)

FOREIGN PATENT DOCUMENTS

| | | |
|---|---|---|
| CA | 2869036 A1 | 10/2013 |
| CA | 2948832 A1 | 11/2015 |

(Continued)

OTHER PUBLICATIONS

PCT Search Report and Written Opinion prepared for PCT Application No. PCT/US2021/046451, completed Oct. 27, 2021.

(Continued)

*Primary Examiner* — Oluwatosin A Ogunbiyi

(74) *Attorney, Agent, or Firm* — Barnes & Thornburg LLP

(57) ABSTRACT

The invention relates to direct-fed microbials for use in *E. coli* inhibition in animals in combination with antibiotics selected from the group consisting of ceftiofur, oxytetracycline, tulathromycin, and lincomycin. More particularly, the invention relates to isolated *Bacillus* strains 2, 3, 4, 5, 9, 57, 71, and 126, and strains having all of the identifying characteristics of these strains, for a use comprising the above-mentioned use.

22 Claims, 13 Drawing Sheets

(56) References Cited

U.S. PATENT DOCUMENTS

| | | | |
|---|---|---|---|
| 2010/0010080 A1 | 1/2010 | Mockett et al. |
| 2010/0062021 A1 | 3/2010 | Winkelman |
| 2010/0092428 A1 | 4/2010 | Schmidt et al. |
| 2010/0291564 A1 | 11/2010 | Stanley et al. |
| 2012/0100118 A1 | 4/2012 | Rehberger et al. |
| 2012/0177620 A1 | 7/2012 | Farmer |
| 2012/0315258 A1 | 12/2012 | Rehberger et al. |
| 2012/0315259 A1 | 12/2012 | Friedlander |
| 2013/0064927 A1 | 3/2013 | Davis et al. |
| 2013/0098837 A1 | 4/2013 | Dash et al. |
| 2013/0100118 A1 | 4/2013 | Mlyniec et al. |
| 2013/0136695 A1 | 5/2013 | Hargis et al. |
| 2013/0216586 A1 | 8/2013 | LeBrun et al. |
| 2013/0295067 A1 | 11/2013 | Baltzley et al. |
| 2014/0106974 A1 | 4/2014 | Sun et al. |
| 2014/0141044 A1 | 5/2014 | Bhatt et al. |
| 2014/0273150 A1 | 9/2014 | Angel |
| 2014/0315716 A1 | 10/2014 | Matheny et al. |
| 2014/0363819 A1 | 12/2014 | Rowlyk et al. |
| 2015/0079058 A1 | 3/2015 | Nielsen et al. |
| 2015/0111214 A1 | 4/2015 | Liu |
| 2015/0147303 A1 | 5/2015 | Hsieh |
| 2015/0216203 A1 | 8/2015 | Isaksen et al. |
| 2015/0216916 A1 | 8/2015 | Galbraith et al. |
| 2015/0250842 A1 | 9/2015 | Calabotta et al. |
| 2016/0100607 A1 | 4/2016 | Schmidt et al. |
| 2016/0108467 A1 | 4/2016 | Semikhodskii et al. |
| 2017/0079308 A1 | 3/2017 | King et al. |
| 2017/0106027 A1 | 4/2017 | Tonda et al. |
| 2017/0166466 A1 | 6/2017 | King et al. |
| 2017/0246224 A1 | 8/2017 | King et al. |
| 2017/0327840 A1 | 11/2017 | Kijlstra et al. |
| 2018/0170968 A1 | 6/2018 | Bralkowski et al. |
| 2018/0361444 A1 | 12/2018 | Franssen et al. |
| 2019/0021341 A1 | 1/2019 | Davis et al. |
| 2019/0201458 A1 | 7/2019 | Frouel et al. |
| 2020/0015497 A1 | 1/2020 | King et al. |
| 2020/0029592 A1 | 1/2020 | King et al. |
| 2020/0093158 A1 | 3/2020 | Calabotta et al. |
| 2020/0281225 A1 | 9/2020 | Kiarie et al. |
| 2020/0359653 A1 | 11/2020 | Johnson et al. |
| 2021/0112815 A1 | 4/2021 | McBride et al. |
| 2021/0154242 A1 | 5/2021 | Keller et al. |
| 2022/0143110 A1 | 5/2022 | Lewis et al. |

FOREIGN PATENT DOCUMENTS

| | | | |
|---|---|---|---|
| CN | 101076585 A | 11/2007 |
| CN | 101159102 A | 4/2008 |
| CN | 101405411 A | 4/2009 |
| CN | 101926830 A | 12/2010 |
| CN | 102223809 A | 10/2011 |
| CN | 103980535 A | 8/2014 |
| CN | 104411182 A | 3/2015 |
| CN | 104735999 A | 6/2015 |
| CN | 106265880 A | 1/2017 |
| CN | 106420841 A | 2/2017 |
| CN | 106714570 A | 5/2017 |
| CN | 107156512 A | * 9/2017 |
| CN | 107841478 A | 3/2018 |
| CN | 108208315 A | 6/2018 |
| CN | 109497281 A | 3/2019 |
| CN | 109561712 A | 4/2019 |
| CN | 110573606 A | 12/2019 |
| CN | 112739358 A | 4/2021 |
| CN | 113164529 A | 7/2021 |
| CN | 113286510 A | 8/2021 |
| EP | 1574564 A1 | 9/2005 |
| GB | 1392813 A | 4/1975 |
| GB | 1434582 A | 5/1976 |
| JP | 2001169760 A | 6/2001 |
| JP | 3417904 B2 | 6/2003 |
| KR | 100427600 B1 | 4/2004 |
| WO | 2005019417 A2 | 3/2005 |
| WO | 2007083147 A2 | 7/2007 |
| WO | 2010/032233 A2 | 3/2010 |
| WO | 20100033714 A1 | 3/2010 |
| WO | 2012/009712 A2 | 1/2012 |
| WO | 2012101528 A2 | 8/2012 |
| WO | 2014020141 A1 | 2/2014 |
| WO | 2014067081 A1 | 5/2014 |
| WO | 20140172520 A1 | 10/2014 |
| WO | 2015057330 A1 | 4/2015 |
| WO | 2015132085 A1 | 9/2015 |
| WO | 2015160960 A1 | 10/2015 |
| WO | 2015175667 A1 | 11/2015 |
| WO | 2017081105 A1 | 5/2017 |
| WO | 2017/151608 A1 | 9/2017 |
| WO | 2018148847 A1 | 8/2018 |
| WO | 2018/167171 A1 | 9/2018 |
| WO | 2019090068 A1 | 5/2019 |
| WO | 2019090088 A1 | 5/2019 |
| WO | WO2019141815 | 7/2019 |
| WO | WO2019152791 | 8/2019 |
| WO | 2019/213243 A1 | 11/2019 |
| WO | 2020069255 A1 | 4/2020 |
| WO | 2020072578 A1 | 4/2020 |
| WO | WO2021035137 | 2/2021 |
| WO | 2021/041603 A1 | 3/2021 |
| WO | 2023018686 A1 | 2/2023 |

OTHER PUBLICATIONS

Abdelwhab et al., "The use of FTA® filter papers for diagnosis of avian influenza virus". J. Virological Meth., 174:120-122, Mar. 17, 2011 (Mar. 17, 2011).

Abutarbush et al. (2004). Jejunal hemorrhage syndrome in 2 Canadian beef cows. Can. Vet. J. 45, 48-50.

Abutarbush et al. (2005). Jejunal hemorrhage syndrome in dairy and beef cattle: 11 cases (2001 to 2003). Can. Vet. J. Rev. Vét. Can. 46, 711-715.

Adaska et al. (2014). Jejunal hematoma in cattle: a retrospective case analysis. J. Vet. Diagn. Investig. Off. Publ. Am. Assoc. Vet. Lab. Diagn. Inc 26, 96-103.

Albini et al. (2010). Real-time multiplex PCR assays for reliable detection of Clostridium perfringens toxin genes in animal isolates, Veterinary Microbiology, 127 (1-2): 179-185.

Bae H.D., Yanke L.J, Cheng K.J., Selinger L.B., 1999, "A novel staining method for detecting phytase activity," Journal of Microbiological Methods, 39:1, 17-22.

Baines et al. (2011). Mouldy feed, mycotoxins and Shiga toxin-producing Escherichia coli colonization associated with Jejunal Hemorrhage Syndrome in beef cattle. BMC Vet. Res. 7, 24.

Bankamp et al., "Improving molecular tools for global surveillance of measles virus". J. Clin. Virology, 58 Sep. 2013 (Sep. 2013).

Byoung-Joo et al. (Acta Vet Beograd, 2017, 67: 153) (Year: 2017).

Canning, et al., "Effect of direct-fed microbial Bacillus subtilis C-3102 on enteric health in nursery pigs after challenge with porcine epidemic diarrhea virus," Journal of Swine Health and Production, May 3, 2017, 25(3): 129-137.

Ceci, L., Paradies, P., Sasanelli, M., De Caprariis, D., Guarda, F., Capucchio, M. t., and Carelli, G. (2006). Haemorrhagic Bowel Syndrome in Dairy Cattle: Possible Role of Clostridium perfringens Type A in the Disease Complex. J. Vet. Med. Ser. A 53, 518-523.

Chen et al, 2013 J of Proteone Research, 12, p. 1151-1161.

Choudhary et al. 2009 (Interactions of Bacillus spp. and plants—with special reference to induced systemic resistance (ISR); Microbiological Research 164: 493-513). (Year:2009).

Cohn et al "Bacillus strains improving health and performance of production animals" ip.com Feb. 11, 2016.

Cranford E. Good Nutrition Vital for Pregnant Cows. NDSU. 2016; 1.

Credille et al. (2014). Prevalence of bacteremia in dairy cattle with acute puerperal metritis. J Vet Intern Med, 28:1606-1612.

De Crignis et al. (J of Virol Methods, 2010, 165, 51-56) (Year: 2010).

Dennison et al. (2002). Hemorrhagic bowel syndrome in dairy cattle: 22 cases (1997-2000). J. Am. Vet. Med. Assoc. 221, 686-689.

(56)          References Cited

OTHER PUBLICATIONS

Dennison et al. (2005). Comparison of the odds of isolation, genotypes, and in vivo production of major toxins by Clostridium perfringens obtained from the gastrointestinal tract of dairy cows with hemorrhagic bowel syndrome or left-displaced abomasum. J. Am. Vet. Med. Assoc. 227, 132-138.

Dobbs et al , 2002 Arch Pathol Lab Med. vol 126, p. 56-63.

EP search report in EP 16789853 completed Aug. 8, 2018.

EPA, Final Risk assessment of Bacillus Subtilis, Feb. 1997, p. 3, 9 (1997).

European Search Report, European Application No. 20855232.3-1105 dated Aug. 31, 2023, 8 pages.

Extended European Search Report, European Application No. 15792802.9-1358 dated Nov. 8, 2017, 8 pages.

Fei et al., "A laboratory landfill simulator for physical, geotechnical, chemical and microbial characterization of solid waste biodegradation processes," Couples Phenomena in Environmental Geotechnics, May 20, 2013 (May 20, 2013), Taylor & Francis Group, London, pp. 321-327.

Frydendahl et al. (2001). Automated 5' nuclease assay for detection of virulence factors in porcine Escherichia coli. Molec.Cell. Probes. 15: 151-160.

Haldar et al., "Development of a haemolysin gene-based multiplex PCR for simultaneous detection of Vibrio campbellii, Vibrio harveyi and Vibrio parahaemolyticus", Letters in Applied Microbiology 50 (2010) 146-152. Epub Nov. 5, 2009.

Harnentis et al. "Isolation, Characterization and Production of Mannanase from Thermophilic Bacteria to Increase the Feed Quality," Pakistan Journal of Nutrition 12 (4): 360-364, 2013.

International Search Report and Written Opinion for Application No. PCT/US23/76159, mailed Apr. 11, 2024.

International search report and written opinion for PCT/US2017/019941, mailed May 26, 2017.

International search report and written opinion for PCT/US2018/058948, mailed Jan. 18, 2019.

International search report and written opinion for PCT/US2019/030182, mailed Aug. 8, 2019.

International search report and written opinion for PCT/US2019/054190, mailed Feb. 10, 2020.

International Search Report prepared for PCT/US2020/047390, mailed Jan. 21, 2021.

International Search Report prepared for PCT/US2020/048101 mailed Jan. 22, 2021.

Jinneman et al. (2003). Multiplex Real-Time PCR Method to Identify Shiga Toxin Genes stx1 and stx2 and Escherichia coli O157:H7/H—Serotype. Appl. Environ. Microbiol. Oct. 2003 vol. 69 No. 10 6327-6333.

Johnson et al. (2012). A MIQE-Compliant Real-Time PCR Assay for Aspergillus Detection., PLOSone., 7(7): 1-8.

Karigar et al., "Role of Microbial Enzymes in the Bioremediation of Pollutants: A Review," Enzyme Research, vol. 2011, Article ID 805187, 11 pages.

Kiarie et al. "The Role of Added Feed Enzymes in Promoting Gut Health in Swine and Poultry," Nutrition Research Reviews, Jun. 1, 2013 (Jun. 1, 2013), vol. 26, pp. 71-88. Entire document.

Krishnani, Genbank entry KJ000877 published Feb. 2014.

La Ragione et al. "Bacillus subtilis Spores Competitively Exclude Escherichia coli O78: K80 in Poultry," Veterinary Microbiology, Mar. 20, 2001 (Mar. 20, 2001). vol. 79, pp. 133-142. Entire document.

Lima et al. (Exp Parasitology, 2012, 132:348-354) (Year: 2012).

Lowe, et al., Nucleic Acids Research, 1990, 18(7) 1757-61.

Mahar et al., "Modeling and simulation of landfill gas production from pretreated MSW landfill simulator," Frontiers of Environmental Science & Engineering, Apr. 15, 2014 (Apr. 15, 2014), vol. 10, Iss. 1, pp. 159-167.

Malinen et al. (2003). Comparison of real-time PCR with SYBR Green I or 5 '-nuclease assays and dot-blot hybridization with rDNA-targeted oligonucleotide probes in quantification of selected faecal bacteria. Microbiology. 149: 269-277.

Mapleton. About our Cows—Producing Milk & Pregnancy. Mapleton's Organic. 2016;1-3.

McClure et al. "Assessment of DNA extracted from FTA® cards for use on the Illumina iSelect Beach Chip," BMC Research Notes, 2009, 2(107) 4 pages.

Miller et al., "Sanitary Landfill Simulation: Test Parameters and a Simulator Conceptual Design," Naval Facilities Engineering Command: Civil Engineering Laboratory, Oct. 20, 1976 (Oct. 20, 1976), pp. 1-47. Retrieved from the Internet: <https://apps.dtic.mil/dtic/tr/fulltext/u2/a030998.pdf>.

Naslund et al. (J. of Virol Methods, 2011, 178: 186-190) (Year: 2011).

Nielsen et al. (2003). Detection and characterization of verocytotoxin-producing Escherichia coli by automated 5 nuclease PCR assay, Journal of ClinicalMicrobiology, vol. 41, No. 7, pp. 2884-2893.

Ou et al., "Identification of HIV-1 infected infants and young children using real-time RT PCR and dried blood spots from Uganda and Cameroon," Journal of Virological Methods, 2007, 144, 109-14.

Paradis et al. (BMC Med Genet, 2010, 11:54) (Year: 2010).

PCT Search Report and Written Opinion for PCT/US2015/030578, completed Jul. 9, 2015.

PCT Search Report and Written Opinion for PCT/US2016/030223, completed Jul. 29, 2016.

PCT Search Report and Written Opinion prepared for PCT/US2020/023586, Jun. 19, 2020.

Peng, et al., "Evaluation of antiviral activity of Bacillus licheniformis-fermented products against porcine epidemic diarrhea virus," AMB Express, Dec. 3, 2019, 9(191): 1-12.

Rajendram et al., Journal of Microbiological Methods, 2006, 67, 582-92.

Ramachandran et al., "A Broad-Spectrum Antimicrobial Activity of Bacillus subtilis RLID 12.1," 2014.

Safitri et al. "Ability of Bacterial Consortium: Bacillus coagulans, Bacilus licheniformis, Bacillus pumilus, Bacillus subtilis, Nitrosomonas sp. and Pseudomonas putida in Bioremediation of Waste Water In; Cisirung Waste Water Treatment Plant," Agrolife Scientific Journal, 2015, vol. 4, No. 1, pp. 146-152.

Schmid, PJ et al. "Bacillus cereus in Packaging Material: Molecular and Phenotypical Diversity Revealed" pp. 1-11. Frontiers in Microbiology. vol. 12. Jul. 12, 2021; abstract; DOI: 10.3389/fmicb.2021.698974.

Schmidt et al., "New Concepts of microbial treatment processes for the nitrogen removal in wastewater," 2003.

Search Report for copending CN Application No. 202080037387.1, mailed Dec. 3, 2023.

Sheldon et al. (2009). Defining postpartum uterine disease and the mechanisms of infection and immunity in the female reproductive tract in cattle. Biol Reprod 81:1025-1032.

Sonune et al., "Isolation, characterization and identification of extracellular enzyme producer Bacillus licheniformis from municipal wastewater and evaluation of the biodegradability," Biotechnology Research and Innovation, Jan.-Dec. 2018, vol. 2, No. 1, pp. 37-44.

Souza et al. J. Anim. Sci. vol. 90, Suppl. 3/J. Dairy Sci. vol. 95, Suppl. 2 T281.

Sumi et al, Antimicrobial peptides of the genus Bacillus: a new era for antibiotics, Nov. 19, 2014, p. 1-7.

Supp. European Search Report, European Application No. 20858946, dated Aug. 23, 2023.

Trotter, "Bacillus Subtillis De111 Intake May Improve Blood Lipids and Endothelial Function in Healthy Adults" pp. 621-630. Beneficial Microbes. vol. 11, No. 7. Nov. 15, 2020; p. 623, p. 626; DOI: 10.3920/BM2020.0039.

Wampfler et al. (Pl-os one, 2013, p. 1-12) (Year: 2013).

West et al. (2007) Rapid Detection of Escherichia coli Virulence Factor Genes using Multiplex Real-Time TaqMan® PCR Assays. Veterinary Microbiology 122(3-4): 323-331.

White et al. (Infection and Immunity, 2014, 82(4):1559-1571) (Year: 2014).

(56) References Cited

OTHER PUBLICATIONS

Yatsuyanagi et al. (2002). Characterization of enteropathogenic and enteroaggregative *Escherichia coli* isolated from diarrheal outbreaks, Journal of Clinical Microbiology, vol. 40, No. 1, pp. 294-297.

Zganjer, et al. Treatment of rectal prolapse in children with cow milk injection sclerotherapy: 30-year experience, World Journal of Gastroanterology, 2008, 14(5) 740-7.

Office Action and Search Report for copending Chinese Patent Application No. 202180069381.7, issued on Apr. 7, 2024.

Yang Minxin, "Research Progress on the Application of Bacillus Amyloliquefaciens in Animal Production", Feed China, No. 6, Jun. 10, 2018.

Extended European Search Report for copending application EP 21859032.1, mailed Jul. 30, 2024.

* cited by examiner

| Pathogen | Pathogen # | Antibiotic | Bs2 | Bs3 | Bs4 |
|----------|------------|------------|----------|----------|----------|
| E.coli | p1 | Lincomix | 82.1946 | 73.4306 | 72.19768 |
| E.coli | p2 | | 6.005222 | -3.00783 | -7.37337 |
| E.coli | p3 | | 75.24952 | 74.87524 | 70.08637 |
| E.coli | p4 | | 72.21788 | 73.42069 | 66.8981 |
| E.coli | p5 | | 71.29838 | 71.63629 | 68.65656 |
| E.coli | p6 | | 77.56103 | 72.18861 | 66.92051 |
| E.coli | p7 | | 70.12535 | 71.99562 | 65.64863 |
| E.coli | p8 | | 77.71893 | 80.29128 | 68.90486 |
| E.coli | p9 | | 64.2878 | 50.94082 | 61.47996 |
| E.coli | p10 | | 73.10659 | 69.28471 | 76.0256 |
| E.coli | p11 | | 67.05975 | 62.1743 | 66.10512 |
| E.coli | p12 | | 68.97663 | 64.81332 | 70.21219 |

FIG. 5

| Bs5 | BS 9 | BS 57 | BS 71 | BS 126 | Anti Control |
|---|---|---|---|---|---|
| 71.44765 | 51.52242 | 74.75674 | 58.67853 | 68.78062 | 3.476546 |
| 10.57963 | 53.81244 | 61.12684 | 63.99416 | 57.31222 | -2.39562 |
| 74.76008 | 35.59696 | 63.13515 | 30.38133 | 42.30045 | 2.914996 |
| 71.32799 | 49.12984 | 70.88915 | 57.86309 | 69.63811 | 8.967736 |
| 73.69445 | 49.9225 | 81.02112 | 63.35981 | 75.9129 | 3.899578 |
| 70.69685 | 54.50631 | 77.08573 | 65.49943 | 76.63516 | 5.469388 |
| 84.4608 | 55.69657 | 78.14117 | 57.71747 | 70.80704 | 31.76215 |
| 78.24853 | 68.15269 | 83.24222 | 72.06409 | 79.7048 | 5.989759 |
| 55.23057 | 37.36075 | 77.87299 | 51.25202 | 65.39889 | 17.33359 |
| 73.07153 | 38.74436 | 81.84698 | 55.44783 | 71.02584 | 1.673736 |
| 66.04897 | 48.62905 | 79.48108 | 57.47791 | 66.3014 | 1.286533 |
| 68.54687 | 48.29853 | 77.51222 | 57.77876 | 64.08016 | 25.82482 |

FIG. 5 (cont'd)

MICROBIAL STRAINS AND ANTIBIOTICS

CROSS-REFERENCE TO RELATED APPLICATIONS

This application is a national stage entry under 35 USC § 371(b) of PCT International Application No. PCT/US2021/046451, filed Aug. 18, 2021, which claims priority under 35 U.S.C. § 119(e) to U.S. Provisional Application Ser. No. 63/068,668 filed on Aug. 21, 2020 the disclosures of both of which are expressly incorporated by reference herein.

FIELD OF THE DISCLOSURE

The invention relates to direct-fed microbials for use in *E. coli* inhibition in animals in combination with an antibiotic selected from the group consisting of ceftiofur, oxytetracycline, tulathromycin, and lincomycin. More particularly, the invention relates to isolated *Bacillus* strains 2, 3, 4, 5, 9, 57, 71, and 126 and strains having all of the identifying characteristics of these strains, for a use comprising the above-mentioned use in combination with an antibiotic selected from the group consisting of ceftiofur, oxytetracycline, tulathromycin, and lincomycin.

BACKGROUND AND SUMMARY OF THE INVENTION

The present invention relates to direct-fed microbial (DFM) compositions and methods for *E. coli* inhibition in an animal. An animal's gastrointestinal tract is constantly challenged by large numbers of bacteria, viruses, fungi, and protozoa found in feed, bedding, and the environment. The gastrointestinal tract has a sophisticated system to counter these potential pathogens consisting of physical, chemical, and immunological lines of defense. Beneficial bacteria are an important part of this system because they provide animals with bacteria that assist in establishment (or reestablishment) of a normal bacterial profile, they strengthen the animal's immune system, and they help to fight disease.

Antibiotic resistance is an increasingly important issue in human medicine, as well as in animal agriculture. The Food and Drug Administration reported that in 2016 the U.S. swine industry purchased about 6.9 million pounds of medically important antibiotics, which emphasizes the importance of preventing the development of antibiotic resistant organisms in the animal agricultural industry. Methods are being developed in an effort to combat antibiotic resistance, but little has been done to utilize synergistic direct-fed microbials (e.g., probiotics) as tools to combat antibiotic resistance.

Applicants have developed direct-fed microbials that result in *E. coli* inhibition in animals in combination with antibiotics selected from the group consisting of ceftiofur, oxytetracycline, tulathromycin, and lincomycin. The direct-fed microbials and antibiotics and compositions comprising the direct-fed microbials and antibiotics described herein offer a commercial benefit by providing *E. coli* inhibition in animals, such as agricultural animals.

Methods are provided for inhibiting *E. coli* in animals. In various embodiments, the animal can be selected from the group consisting of a poultry species, a porcine species, a caprine species, a bovine species, an ovine species, an equine species, and a companion animal. In the embodiment where the animal is a poultry species, the poultry species can be selected from the group consisting of a broiler, a chicken, a layer, a breeder, a turkey, a turkey poult, a gosling, a duckling, a guineakeet, a pullet, a hen, a rooster, a cockerel, and a capon. In the embodiment where the animal is a porcine species, the porcine species can be selected from the group consisting of a grow finish pig, a nursery pig, a sow, and a breeding stock pig.

In one embodiment, a method of feeding an animal is provided. The method comprises the steps of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering to the animal an antibiotic, wherein the *Bacillus* strain and the antibiotic cause *E. coli* inhibition in the animal and wherein the antibiotic is selected from the group consisting of ceftiofur, oxytetracycline, tulathromycin, and lincomycin.

In another embodiment, a method of controlling a detrimental effect of *E. coli* is provided. The method comprises the steps of administering to an animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering an antibiotic to the animal, and controlling the detrimental effect of *E. coli* in the animal and wherein the antibiotic is selected from the group consisting of ceftiofur, oxytetracycline, tulathromycin, and lincomycin.

In yet another embodiment, a method of feeding an animal is provided. The method comprises the step of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering to the animal an antibiotic wherein the antibiotic is selected from the group consisting of ceftiofur, oxytetracycline, tulathromycin, and lincomycin.

The following clauses, and combinations thereof, provide various additional illustrative aspects of the invention described herein. The various embodiments described in any other section of this patent application, including the section titled "DETAILED DESCRIPTION OF ILLUSTRATIVE EMBODIMENTS" and the EXAMPLES are applicable to any of the following embodiments of the invention described in the numbered clauses below.

1. A method of feeding an animal, the method comprising the steps of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering to the animal an antibiotic, wherein the *Bacillus* strain and the antibiotic cause *E. coli* inhibition in the animal and wherein the antibiotic is selected from the group consisting of ceftiofur, oxytetracycline, tulathromycin, and lincomycin.

2. The method of clause 1 wherein the animal is selected from the group consisting of a poultry species, a porcine species, a caprine species, a bovine species, an ovine species, an equine species, and a companion animal.

3. The method of any one of clauses 1 to 2 wherein the *E. coli* inhibition prevents *E. coli* disease in the animal.

4. The method of any one of clauses 1 to 2 wherein the *E. coli* inhibition reduces *E. coli* disease in the animal.

5. The method of any one of clauses 1 to 4 wherein the animal is a porcine species and the porcine species is selected from the group consisting of a grow finish pig, a nursery pig, a sow, and a breeding stock pig.

6. The method of any one of clauses 1 to 5 wherein the *Bacillus* strain produces an enzyme selected from the group consisting of an α-galactosidase, a protease, a lipase, an amylase, a xylanase, a cellulase, and combinations thereof.

7. The method of any one of clauses 1 to 6 further comprising the step of administering to the animal another different bacterial strain selected from the group consisting of another *Bacillus* strain, a lactic acid bacterial strain, and combinations thereof.

8. The method of any one of clauses 1 to 7 wherein the strain administered is *Bacillus* strain 2 (NRRL No. B-67709).

9. The method of any one of clauses 1 to 7 wherein the strain administered is *Bacillus* strain 3 (NRRL No. B-67710).

10. The method of any one of clauses 1 to 7 wherein the strain administered is *Bacillus* strain 4 (NRRL No. B-67711).

11. The method of any one of clauses 1 to 7 wherein the strain administered is *Bacillus* strain 5 (NRRL No. B-67712).

12. The method of any one of clauses 1 to 11 wherein the *Bacillus* strain is administered in the feed composition at a dose of about $1.0 \times 10^3$ CFU/gram of the feed composition to about $5.0 \times 10^{12}$ CFU/gram of the feed composition.

13. The method of any one of clauses 1 to 11 wherein the *Bacillus* strain is administered in the feed composition at a dose of about $1.0 \times 10^3$ CFU/gram of the feed composition to about $1.0 \times 10^7$ CFU/gram of the feed composition.

14. The method of any one of clauses 1 to 11 wherein the *Bacillus* strain is administered in the feed composition at a dose greater than about $7.0 \times 10^4$ CFU/gram of the feed composition.

15. The method of any one of clauses 1 to 14 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

16. The method of any one of clauses 1 to 15 wherein the animal is a sow and the *Bacillus* strain is administered during lactation.

17. The method of any one of clauses 1 to 15 wherein the animal is a sow and the *Bacillus* strain is administered during gestation.

18. The method of any one of clauses 1 to 17 wherein the feed composition is administered daily to the animal.

19. The method of clause 1 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

20. A method of controlling a detrimental effect of *E. coli*, the method comprising the steps of administering to an animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering an antibiotic to the animal, and controlling the detrimental effect of *E. coli* in the animal wherein the antibiotic is selected from the group consisting of ceftiofur, oxytetracycline, tulathromycin, and lincomycin.

21. The method of clause 20 wherein the animal is selected from the group consisting of a poultry species, a porcine species, a caprine species, a bovine species, an ovine species, an equine species, and a companion animal.

22. The method of any one of clauses 20 to 21 wherein controlling the detrimental effect of the *E. coli* is inhibiting *E. coli* disease in the animal.

23. The method of any one of clauses 20 to 21 wherein controlling the detrimental effect of the *E. coli* is reducing *E. coli* disease in the animal.

24. The method of any one of clauses 20 to 23 wherein the animal is a porcine species and the porcine species is selected from the group consisting of a grow finish pig, a nursery pig, a sow, and a breeding stock pig.

25. The method of any one of clauses 20 to 24 wherein the *Bacillus* strain produces an enzyme selected from the group consisting of an α-galactosidase, a protease, a lipase, an amylase, a xylanase, a cellulase, and combinations thereof.

26. The method of any one of clauses 20 to 25 further comprising the step of administering to the animal another different bacterial strain selected from the group consisting of another *Bacillus* strain, a lactic acid bacterial strain, and combinations thereof.

27. The method of any one of clauses 20 to 26 wherein the strain administered is *Bacillus* strain 2 (NRRL No. B-67709).

28. The method of any one of clauses 20 to 26 wherein the strain administered is *Bacillus* strain 3 (NRRL No. B-67710).

29. The method of any one of clauses 20 to 26 wherein the strain administered is *Bacillus* strain 4 (NRRL No. B-67711).

30. The method of any one of clauses 20 to 26 wherein the strain administered is *Bacillus* strain 5 (NRRL No. B-67712).

31. The method of any one of clauses 20 to 30 wherein the *Bacillus* strain is administered in the feed composition at a dose of about $1.0 \times 10^3$ CFU/gram of the feed composition to about $5.0 \times 10^{12}$ CFU/gram of the feed composition.

32. The method of any one of clauses 20 to 30 wherein the *Bacillus* strain is administered in the feed composition at a dose of about $1.0 \times 10^3$ CFU/gram of the feed composition to about $1.0 \times 10^7$ CFU/gram of the feed composition.

33. The method of any one of clauses 20 to 30 wherein the *Bacillus* strain is administered in the feed composition at a dose greater than about $7.0 \times 10^4$ CFU/gram of the feed composition.

34. The method of any one of clauses 20 to 33 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

35. The method of any one of clauses 20 to 34 wherein the animal is a sow and the *Bacillus* strain is administered during lactation.

36. The method of any one of clauses 20 to 34 wherein the animal is a sow and the *Bacillus* strain is administered during gestation.

37. The method of any one of clauses 20 to 36 wherein the feed composition is administered daily to the animal.

38. The method of clause 20 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

39. A method of feeding an animal, the method comprising the step of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering to the animal an antibiotic wherein the antibiotic is selected from the group consisting of ceftiofur, oxytetracycline, tulathromycin, and lincomycin.

40. The method of clause 39 wherein the animal is selected from the group consisting of a poultry species, a porcine species, a caprine species, a bovine species, an ovine species, an equine species, and a companion animal.

41. The method of any one of clauses 39 to 40 wherein the animal is a porcine species and the porcine species is selected from the group consisting of a grow finish pig, a nursery pig, a sow, and a breeding stock pig.

42. The method of any one of clauses 39 to 41 wherein the *Bacillus* strain produces an enzyme selected from the group consisting of an α-galactosidase, a protease, a lipase, an amylase, a xylanase, a cellulase, and combinations thereof.

43. The method of any one of clauses 39 to 42 further comprising the step of administering to the animal another different bacterial strain selected from the group consisting of another *Bacillus* strain, a lactic acid bacterial strain, and combinations thereof.

44. The method of any one of clauses 39 to 43 wherein the strain administered is *Bacillus* strain 2 (NRRL No. B-67709).

45. The method of any one of clauses 39 to 43 wherein the strain administered is *Bacillus* strain 3 (NRRL No. B-67710).

46. The method of any one of clauses 39 to 43 wherein the strain administered is *Bacillus* strain 4 (NRRL No. B-67711).

47. The method of any one of clauses 39 to 43 wherein the strain administered is *Bacillus* strain 5 (NRRL No. B-67712).

48. The method of any one of clauses 39 to 47 wherein the *Bacillus* strain is administered in the feed composition at a dose of about $1.0\times10^3$ CFU/gram of the feed composition to about $5.0\times10^{12}$ CFU/gram of the feed composition.

49. The method of any one of clauses 39 to 47 wherein the *Bacillus* strain is administered in the feed composition at a dose of about $1.0\times10^3$ CFU/gram of the feed composition to about $1.0\times10^7$ CFU/gram of the feed composition.

50. The method of any one of clauses 39 to 47 wherein the *Bacillus* strain is administered in the feed composition at a dose greater than about $7.0\times10^4$ CFU/gram of the feed composition.

51. The method of any one of clauses 39 to 50 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

52. The method of any one of clauses 39 to 51 wherein the animal is a sow and the *Bacillus* strain is administered during lactation.

53. The method of any one of clauses 39 to 51 wherein the animal is a sow and the *Bacillus* strain is administered during gestation.

54. The method of any one of clauses 39 to 53 wherein the feed composition is administered daily to the animal.

55. The method of clause 39 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

56. The method of any one of clauses 1 to 55 wherein the *Bacillus* strain has an effect selected from the group consisting of maintaining microbial balance in the gut of the animal, improving animal performance or health, maintaining gut health in the animal, reducing detrimental pathogens in the gut of the animal, odor reduction, reducing detrimental pathogens in the urine or feces of the animal, and preserving the growth of beneficial bacteria in the gut of the animal.

57. The method of any one of clauses 1 to 7, 12 to 26, 31 to 43, or 48 to 56 wherein the strain administered is *Bacillus* strain 9 (NRRL No. B-67866).

58. The method of any one of clauses 1 to 7, 12 to 26, 31 to 43, or 48 to 56 wherein the strain administered is *Bacillus* strain 57 (NRRL No. B-67870).

59. The method of any one of clauses 1 to 7, 12 to 26, 31 to 43, or 48 to 56 wherein the strain administered is *Bacillus* strain 71 (NRRL No. B-67867).

60. The method of any one of clauses 1 to 7, 12 to 26, 31 to 43, or 48 to 56 wherein the strain administered is *Bacillus* strain 126 (NRRL No. B-67868).

BRIEF DESCRIPTION OF THE DRAWINGS

FIG. 5 is a heat map of percent inhibition values from all 12 Lincomix-resistant *E. coli* showing an effective inhibition response when eight *Bacillus* supernatants are used in place of Lincomix.

DETAILED DESCRIPTION OF ILLUSTRATIVE EMBODIMENTS

Figure 1A:
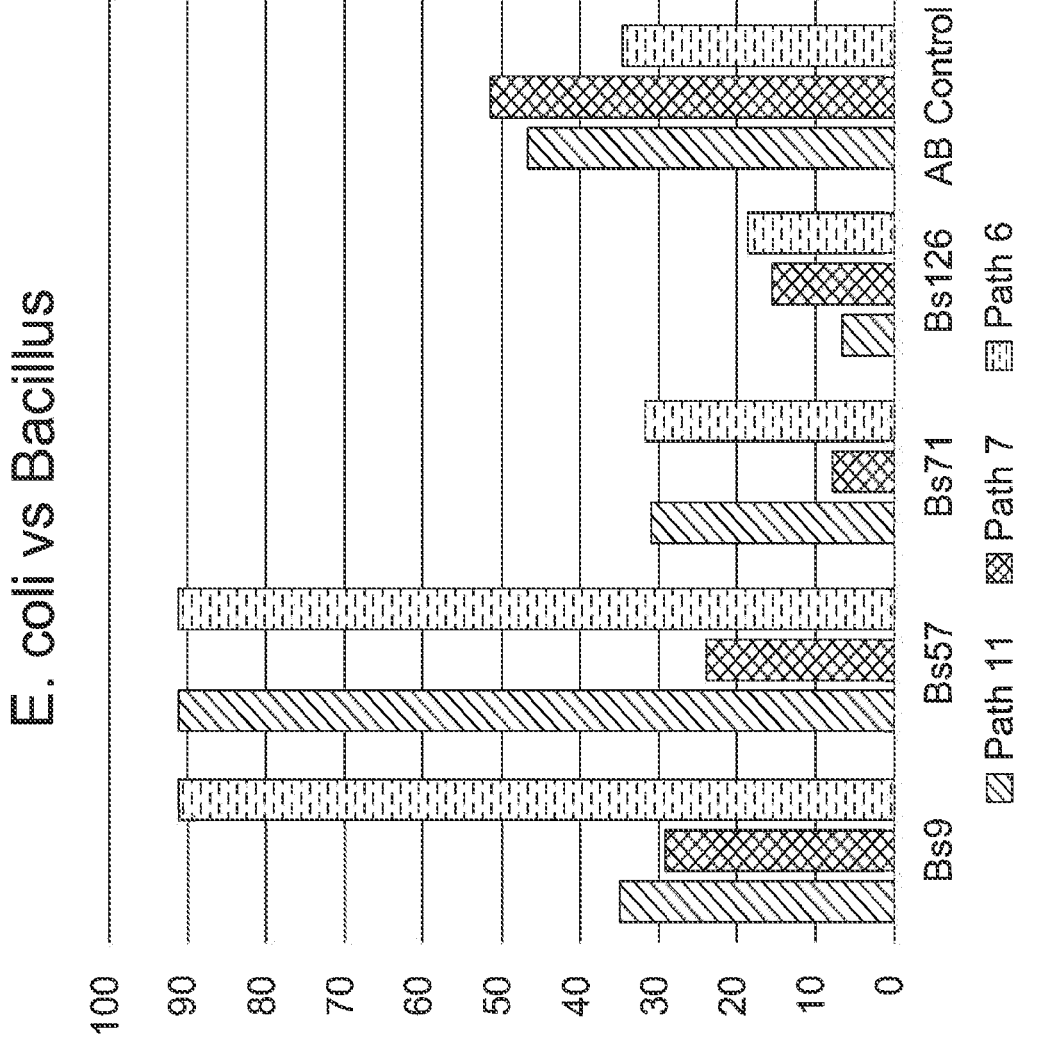
FIGS. 1A-B show percent inhibition values from 3 of 12 *E. coli* showing an improved inhibition response when *Bacillus* supernatant and Ceftiofur are combined.
Figure 1B:
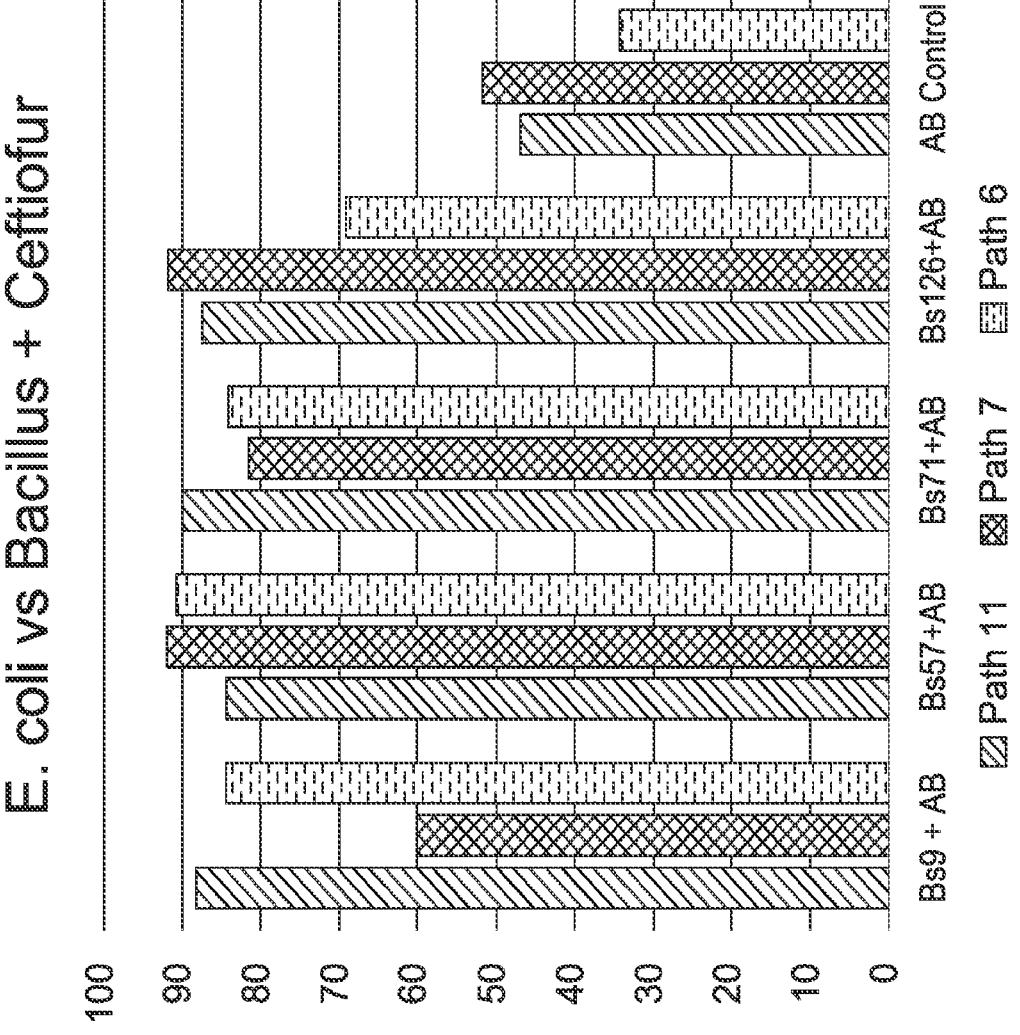
Figure 2A:
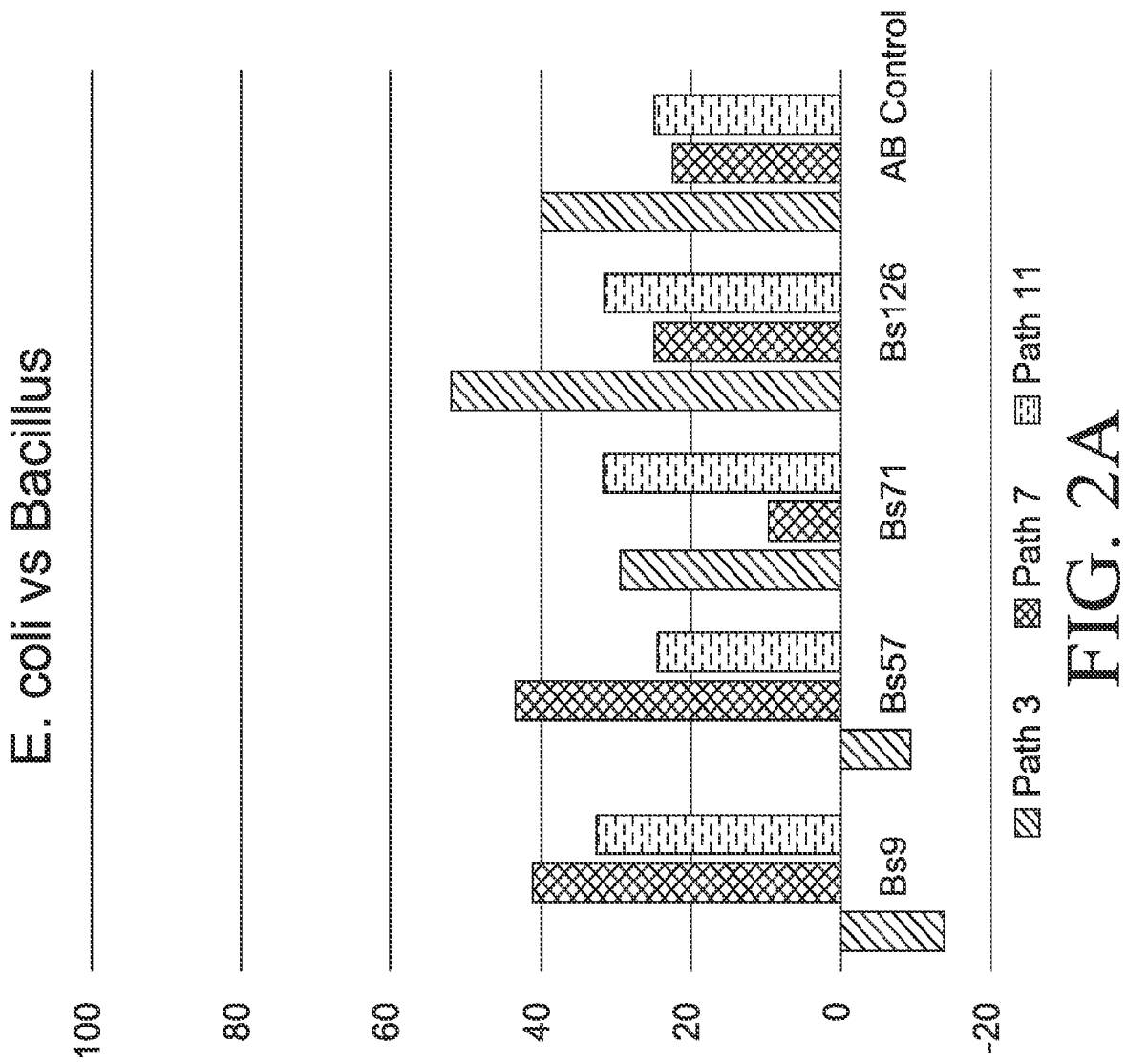
FIGS. 2A-B show percent inhibition values from 3 of 12 *E. coli* showing an improved inhibition response when *Bacillus* supernatant and Oxytetracycline are combined.
Figure 2B:
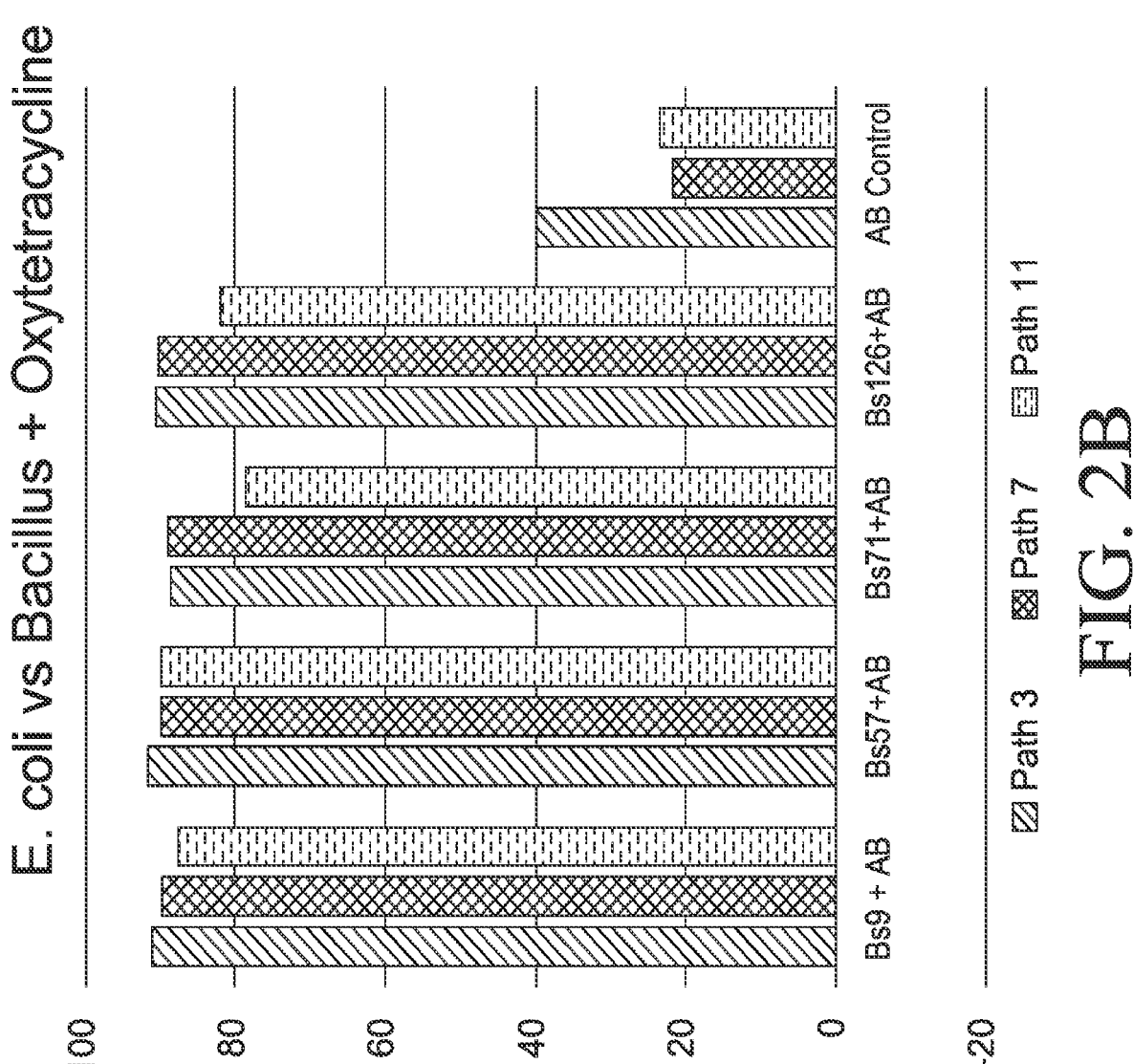
Figure 3A:
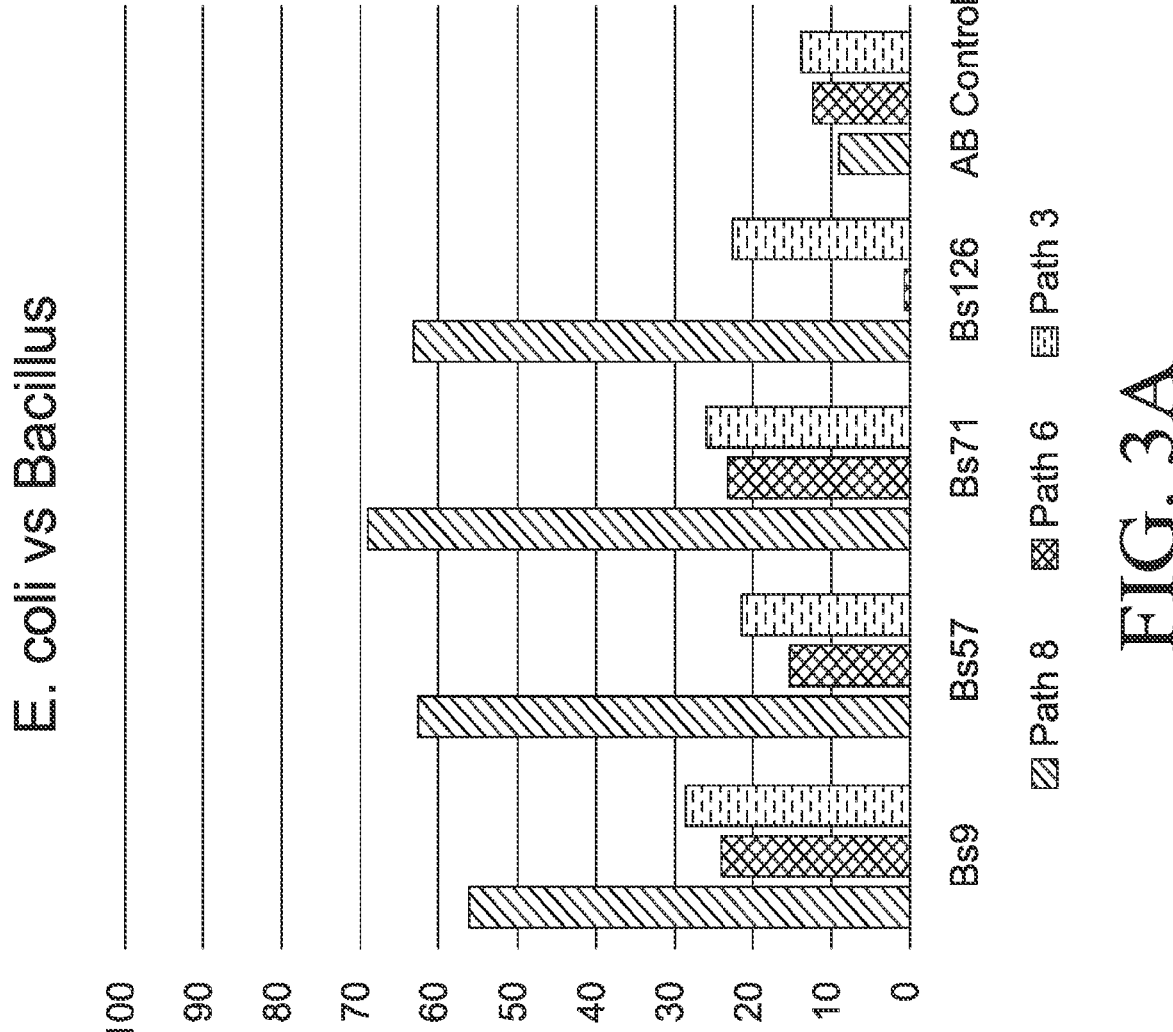
FIGS. 3A-B show percent inhibition values from 3 of 8 *E. coli* showing an improved inhibition response when *Bacillus* supernatant and Tulathromycin are combined.
Figure 3B:
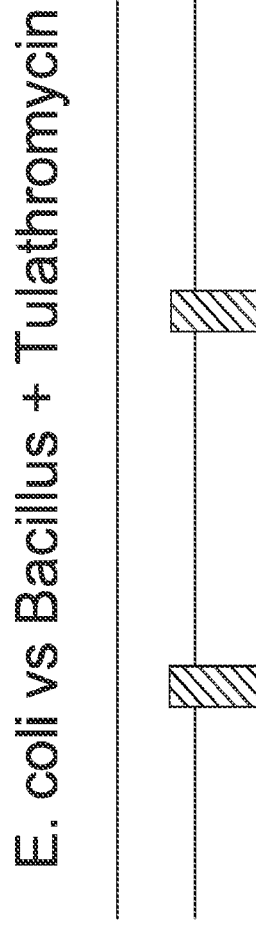
Figure 3B:
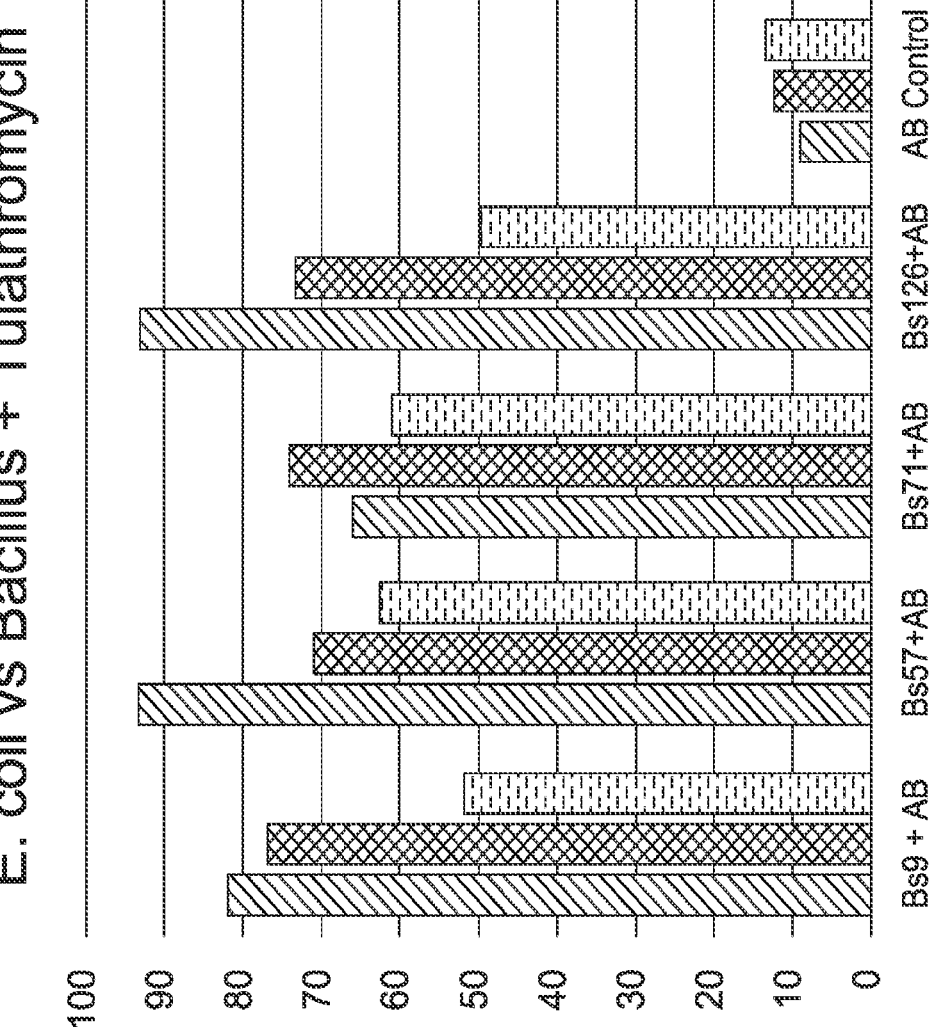
Figure 4A:
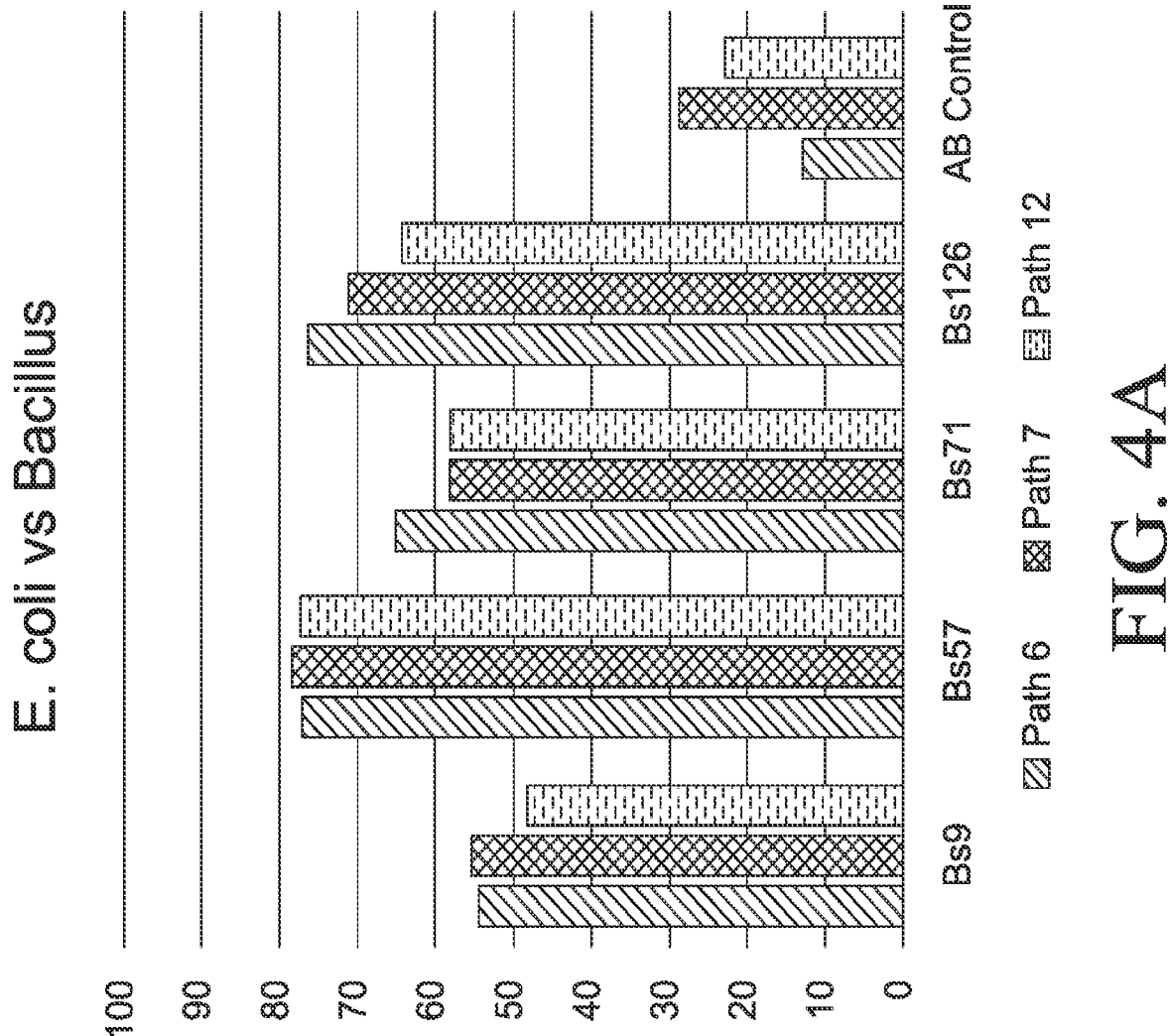
FIGS. 4A-B show percent inhibition values from 3 of 12 *E. coli* showing an improved inhibition response when *Bacillus* supernatant and Lincomycin are combined.
Figure 4B:
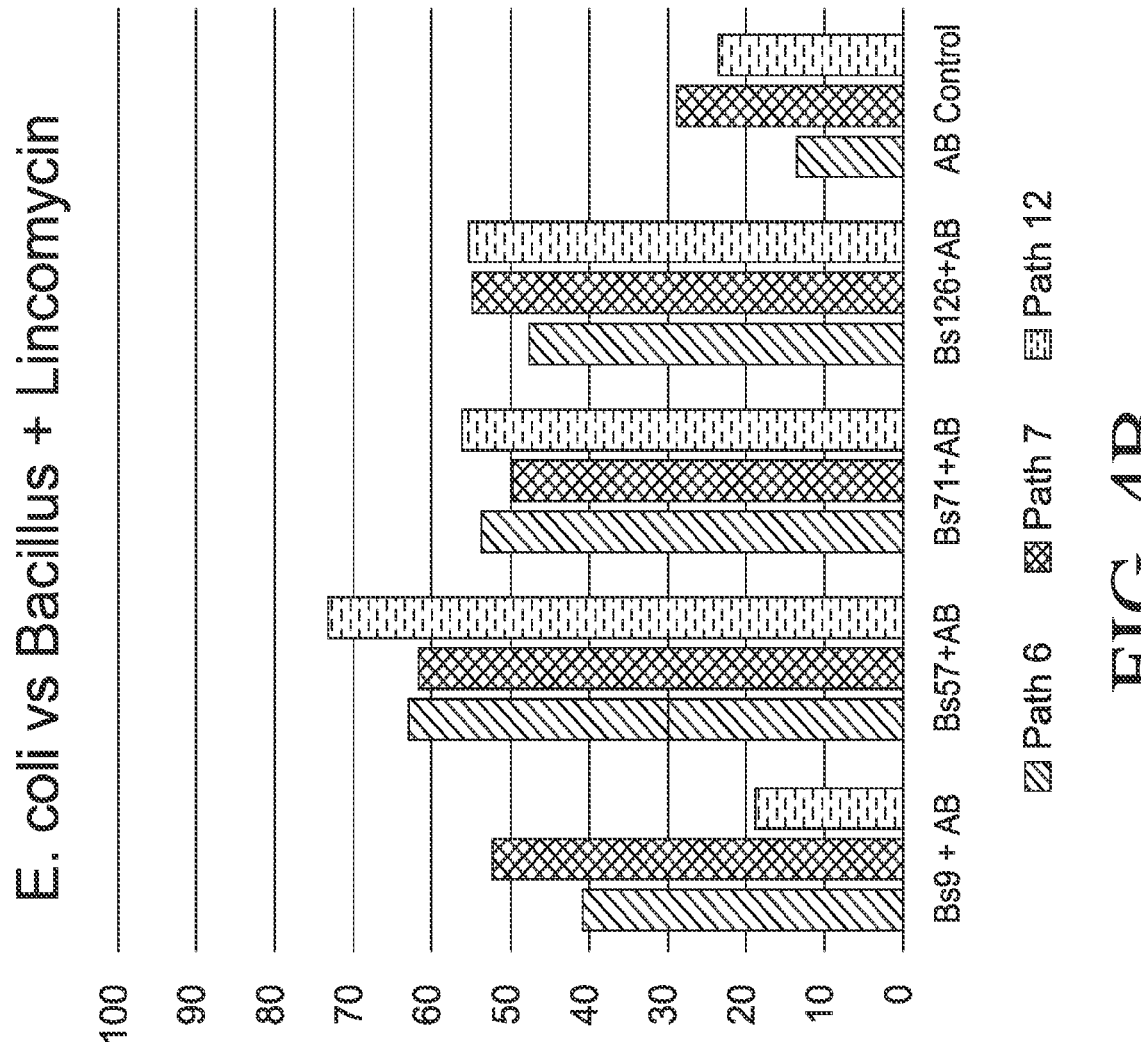

Methods are provided for inhibiting *E. coli* in animals. In various embodiments, the animal can be selected from the group consisting of a poultry species, a porcine species, a caprine species, a bovine species, an ovine species, an equine species, and a companion animal. In the embodiment where the animal is a poultry species, the poultry species can be selected from the group consisting of a broiler, a chicken, a layer, a breeder, a turkey, a turkey poult, a gosling, a duckling, a guineakeet, a pullet, a hen, a rooster, a cockerel, and a capon. In the embodiment where the animal is a porcine species, the porcine species can be selected from the group consisting of a grow finish pig, a nursery pig, a sow, and a breeding stock pig.

In one embodiment, a method of feeding an animal is provided. The method comprises the steps of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering to the animal an antibiotic, wherein the *Bacillus* strain and the antibiotic cause *E. coli* inhibition in the animal.

In another embodiment, a method of controlling a detrimental effect of *E. coli* is provided. The method comprises the steps of administering to an animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering an antibiotic to the animal, and controlling the detrimental effect of *E. coli* in the animal.

In yet another embodiment, a method of feeding an animal is provided. The method comprises the step of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

The following clauses, and combinations thereof, provide various additional illustrative aspects of the invention described herein. The various embodiments described in this section titled "DETAILED DESCRIPTION OF ILLUS-TRATIVE EMBODIMENTS" are applicable to any of the following embodiments of the invention described in the numbered clauses below.

1. A method of feeding an animal, the method comprising the steps of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering to the animal an antibiotic, wherein the *Bacillus* strain and the antibiotic cause *E. coli* inhibition in the animal and wherein the antibiotic is selected from the group consisting of ceftiofur, oxytetracycline, tulathromycin, and lincomycin.

2. The method of clause 1 wherein the animal is selected from the group consisting of a poultry species, a porcine species, a caprine species, a bovine species, an ovine species, an equine species, and a companion animal.

3. The method of any one of clauses 1 to 2 wherein the *E. coli* inhibition prevents *E. coli* disease in the animal.

4. The method of any one of clauses 1 to 2 wherein the *E. coli* inhibition reduces *E. coli* disease in the animal.

5. The method of any one of clauses 1 to 4 wherein the animal is a porcine species and the porcine species is selected from the group consisting of a grow finish pig, a nursery pig, a sow, and a breeding stock pig.

6. The method of any one of clauses 1 to 5 wherein the *Bacillus* strain produces an enzyme selected from the group consisting of an α-galactosidase, a protease, a lipase, an amylase, a xylanase, a cellulase, and combinations thereof.

7. The method of any one of clauses 1 to 6 further comprising the step of administering to the animal another different bacterial strain selected from the group consisting of another *Bacillus* strain, a lactic acid bacterial strain, and combinations thereof.

8. The method of any one of clauses 1 to 7 wherein the strain administered is *Bacillus* strain 2 (NRRL No. B-67709).

9. The method of any one of clauses 1 to 7 wherein the strain administered is *Bacillus* strain 3 (NRRL No. B-67710).

10. The method of any one of clauses 1 to 7 wherein the strain administered is *Bacillus* strain 4 (NRRL No. B-67711).

11. The method of any one of clauses 1 to 7 wherein the strain administered is *Bacillus* strain 5 (NRRL No. B-67712).

12. The method of any one of clauses 1 to 11 wherein the *Bacillus* strain is administered in the feed composition at a dose of about $1.0 \times 10^3$ CFU/gram of the feed composition to about $5.0 \times 10^{12}$ CFU/gram of the feed composition.

13. The method of any one of clauses 1 to 11 wherein the *Bacillus* strain is administered in the feed composition at a dose of about $1.0 \times 10^3$ CFU/gram of the feed composition to about $1.0 \times 10^7$ CFU/gram of the feed composition.

14. The method of any one of clauses 1 to 11 wherein the *Bacillus* strain is administered in the feed composition at a dose greater than about $7.0 \times 10^4$ CFU/gram of the feed composition.

15. The method of any one of clauses 1 to 14 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

16. The method of any one of clauses 1 to 15 wherein the animal is a sow and the *Bacillus* strain is administered during lactation.

17. The method of any one of clauses 1 to 15 wherein the animal is a sow and the *Bacillus* strain is administered during gestation.

18. The method of any one of clauses 1 to 17 wherein the feed composition is administered daily to the animal.

19. The method of clause 1 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

20. A method of controlling a detrimental effect of *E. coli*, the method comprising the steps of administering to an animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering an antibiotic to the animal, and controlling the detrimental effect of *E. coli* in the animal wherein the antibiotic is selected from the group consisting of ceftiofur, oxytetracycline, tulathromycin, and lincomycin.

21. The method of clause 20 wherein the animal is selected from the group consisting of a poultry species, a porcine species, a caprine species, a bovine species, an ovine species, an equine species, and a companion animal.

22. The method of any one of clauses 20 to 21 wherein controlling the detrimental effect of the *E. coli* is inhibiting *E. coli* disease in the animal.

23. The method of any one of clauses 20 to 21 wherein controlling the detrimental effect of the *E. coli* is reducing *E. coli* disease in the animal.

24. The method of any one of clauses 20 to 23 wherein the animal is a porcine species and the porcine species is selected from the group consisting of a grow finish pig, a nursery pig, a sow, and a breeding stock pig.

25. The method of any one of clauses 20 to 24 wherein the *Bacillus* strain produces an enzyme selected from the group consisting of an α-galactosidase, a protease, a lipase, an amylase, a xylanase, a cellulase, and combinations thereof.

26. The method of any one of clauses 20 to 25 further comprising the step of administering to the animal another different bacterial strain selected from the group consisting of another *Bacillus* strain, a lactic acid bacterial strain, and combinations thereof.

27. The method of any one of clauses 20 to 26 wherein the strain administered is *Bacillus* strain 2 (NRRL No. B-67709).

28. The method of any one of clauses 20 to 26 wherein the strain administered is *Bacillus* strain 3 (NRRL No. B-67710).

29. The method of any one of clauses 20 to 26 wherein the strain administered is *Bacillus* strain 4 (NRRL No. B-67711).

30. The method of any one of clauses 20 to 26 wherein the strain administered is *Bacillus* strain 5 (NRRL No. B-67712).

31. The method of any one of clauses 20 to 30 wherein the *Bacillus* strain is administered in the feed composition at a dose of about $1.0 \times 10^3$ CFU/gram of the feed composition to about $5.0 \times 10^{12}$ CFU/gram of the feed composition.

32. The method of any one of clauses 20 to 30 wherein the *Bacillus* strain is administered in the feed composition at a dose of about $1.0 \times 10^3$ CFU/gram of the feed composition to about $1.0 \times 10^7$ CFU/gram of the feed composition.

33. The method of any one of clauses 20 to 30 wherein the *Bacillus* strain is administered in the feed composition at a dose greater than about $7.0 \times 10^4$ CFU/gram of the feed composition.

34. The method of any one of clauses 20 to 33 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

35. The method of any one of clauses 20 to 34 wherein the animal is a sow and the *Bacillus* strain is administered during lactation.

36. The method of any one of clauses 20 to 34 wherein the animal is a sow and the *Bacillus* strain is administered during gestation.

37. The method of any one of clauses 20 to 36 wherein the feed composition is administered daily to the animal.

38. The method of clause 20 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

39. A method of feeding an animal, the method comprising the step of administering to the animal a feed composition or drinking water comprising an effective amount of an additive comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, and administering to the animal an antibiotic wherein the antibiotic is selected from the group consisting of ceftiofur, oxytetracycline, tulathromycin, and lincomycin.

40. The method of clause 39 wherein the animal is selected from the group consisting of a poultry species, a porcine species, a caprine species, a bovine species, an ovine species, an equine species, and a companion animal.

41. The method of any one of clauses 39 to 40 wherein the animal is a porcine species and the porcine species is selected from the group consisting of a grow finish pig, a nursery pig, a sow, and a breeding stock pig.

42. The method of any one of clauses 39 to 41 wherein the *Bacillus* strain produces an enzyme selected from the group consisting of an α-galactosidase, a protease, a lipase, an amylase, a xylanase, a cellulase, and combinations thereof.

43. The method of any one of clauses 39 to 42 further comprising the step of administering to the animal another different bacterial strain selected from the group consisting of another *Bacillus* strain, a lactic acid bacterial strain, and combinations thereof.

44. The method of any one of clauses 39 to 43 wherein the strain administered is *Bacillus* strain 2 (NRRL No. B-67709).

45. The method of any one of clauses 39 to 43 wherein the strain administered is *Bacillus* strain 3 (NRRL No. B-67710).

46. The method of any one of clauses 39 to 43 wherein the strain administered is *Bacillus* strain 4 (NRRL No. B-67711).

47. The method of any one of clauses 39 to 43 wherein the strain administered is *Bacillus* strain 5 (NRRL No. B-67712).

48. The method of any one of clauses 39 to 47 wherein the *Bacillus* strain is administered in the feed composition at a dose of about $1.0 \times 10^3$ CFU/gram of the feed composition to about $5.0 \times 10^{12}$ CFU/gram of the feed composition.

49. The method of any one of clauses 39 to 47 wherein the *Bacillus* strain is administered in the feed composition at a dose of about $1.0 \times 10^3$ CFU/gram of the feed composition to about $1.0 \times 10^7$ CFU/gram of the feed composition.

50. The method of any one of clauses 39 to 47 wherein the *Bacillus* strain is administered in the feed composition at a dose greater than about $7.0 \times 10^4$ CFU/gram of the feed composition.

51. The method of any one of clauses 39 to 50 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

52. The method of any one of clauses 39 to 51 wherein the animal is a sow and the *Bacillus* strain is administered during lactation.

53. The method of any one of clauses 39 to 51 wherein the animal is a sow and the *Bacillus* strain is administered during gestation.

54. The method of any one of clauses 39 to 53 wherein the feed composition is administered daily to the animal.

55. The method of clause 39 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

56. The method of any one of clauses 1 to 55 wherein the *Bacillus* strain has an effect selected from the group consisting of maintaining microbial balance in the gut of the animal, improving animal performance or health, maintaining gut health in the animal, reducing detrimental pathogens in the gut of the animal, odor reduction, reducing detrimental pathogens in the urine or feces of the animal, and preserving the growth of beneficial bacteria in the gut of the animal.

57. The method of any one of clauses 1 to 7, 12 to 26, 31 to 43, or 48 to 56 wherein the strain administered is *Bacillus* strain 9 (NRRL No. B-67866).

58. The method of any one of clauses 1 to 7, 12 to 26, 31 to 43, or 48 to 56 wherein the strain administered is *Bacillus* strain 57 (NRRL No. B-67870).

59. The method of any one of clauses 1 to 7, 12 to 26, 31 to 43, or 48 to 56 wherein the strain administered is *Bacillus* strain 71 (NRRL No. B-67867).

60. The method of any one of clauses 1 to 7, 12 to 26, 31 to 43, or 48 to 56 wherein the strain administered is *Bacillus* strain 126 (NRRL No. B-67868).

In various embodiments, the animal to which a feed additive, a feed composition, or drinking water, and an antibiotic, as described herein is administered can be selected from the group consisting of a poultry species, a porcine species, a caprine species, a bovine species, an ovine species, an equine species, and a companion animal. In the embodiment where the animal is a companion animal, the companion animal can be, for example, a canine species or a feline species. In the embodiment where the animal is a porcine species, the porcine species can be selected from the group consisting of a grow finish pig, a nursery pig, a sow, and a breeding stock pig. In various exemplary embodiments, the animal can be selected from the group consisting of a chicken (e.g., a broiler or a layer), a pig, a horse, a pony, a cow, a turkey, a goat, a sheep, a quail, a pheasant, an ostrich, a duck, a fish (e.g., a tilapia, a catfish, a flounder, or a salmon), a crustacean (e.g., a shrimp or a crab), and combinations thereof. In another embodiment, the feed additive, feed composition, or drinking water, and the antibiotic, as described herein, can be administered to an animal and the animal is a human.

In various embodiments of the methods or compositions described herein, the *Bacillus* strain and the antibiotic, selected from the group consisting of ceftiofur, oxytetracycline, tulathromycin, and lincomycin, can have an effect selected from the group consisting of maintaining microbial balance in the gut of the animal, preventing or reducing *E. coli* disease in the animal, improving animal performance or health, maintaining gut health in the animal, reducing detrimental pathogens in the gut of the animal, odor reduction, reducing detrimental pathogens in the urine or feces of the animal, and preserving the growth of beneficial bacteria in the gut of the animal. In any of the embodiments described herein, the *Bacillus* strain can be a *Bacillus* subtilis strain (e.g., strains 2, 3, 9, 57, 71, and/or 126) or a *Bacillus* licheniformis strain (e.g., strains 4 and 5).

In any embodiments described herein, the *Bacillus* strains can be administered in any combination, with antibiotics selected from the group consisting of ceftiofur, oxytetracycline, tulathromycin, and lincomycin, or can be in the form of any composition described herein. In one embodiment, the strain or strains are administered with an antibiotic selected from the group consisting of ceftiofur, oxytetracycline, tulathromycin, and lincomycin in the same or separate compositions. The *Bacillus* strains described herein, with antibiotics selected from the group consisting of ceftiofur, oxytetracycline, tulathromycin, and lincomycin, can also be used in combination with other different microbial strains, including other *Bacillus* strains or *Lactobacillus* strains.

In one embodiment of the invention, an effective amount of the *Bacillus* strain can be administered to inhibit *E. coli* in the animal. As used herein, "inhibit *E. coli*" can mean reducing *E. coli* disease, preventing *E. coli* disease, maintaining the normal microbial balance in the animal, reducing the number of detrimental *E. coli* organisms in the animal, reducing the activity of *E. coli* in the animal, or reducing the symptoms of *E. coli* disease in the animal, or combinations thereof. By "effective amount" is meant an amount of the *Bacillus* strain (e.g., strain 2, 3, 4, 5, 9, 57, 71, and 126) capable of *E. coli* inhibition or capable of controlling a detrimental effect of *E. coli*, as described below, by any mechanism.

In embodiments described herein wherein the compositions of the present invention comprising *Bacillus* strains 2, 3, 4, 5, 9, 57, 71, and/or 126, or strains having their identifying characteristics, with antibiotics selected from the group consisting of ceftiofur, oxytetracycline, tulathromycin, and lincomycin are administered to an animal, the compositions are preferably administered to animals orally in a feed composition or in drinking water, but any other effective method of administration known to those skilled in the art may be utilized such as in a paste, a gel, a liquid drench, a top dress, a powder, a liquid, or a capsule. In one illustrative embodiment, the *Bacillus* strains 2, 3, 4, 5, 9, 57, 71, and/or 126, or strains having their identifying characteristics, and the antibiotics selected from the group consisting of ceftiofur, oxytetracycline, tulathromycin, and lincomycin, are provided in the form of an additive for addition to the drinking water of an animal.

In another illustrative embodiment, the *Bacillus* strains 2, 3, 4, 5, 9, 57, 71, and/or 126, or strains having their identifying characteristics, and the antibiotics selected from the group consisting of ceftiofur, oxytetracycline, tulathromycin, and lincomycin, are provided in the form of a feed additive for addition to a feed composition. The feed composition may contain *Bacillus* strain 2, 3, 4, 5, 9, 57, 71, and/or 126, or strains having their identifying characteristics, in a mixture with an animal feed blend, including any art-recognized animal feed blend or any animal feed blend described herein. As used herein, "feed composition" or "animal feed composition" means a feed composition comprising *Bacillus* strain 2, 3, 4, 5, 9, 57, 71, and/or 126, or strains having their identifying characteristics, in a mixture with an animal feed blend, and, optionally any other components that could be used in a feed composition, including other bacterial strains, such as other different *Bacillus* strains or *Lactobacillus* strains. In one embodiment, the feed composition may be in the form of a ground meal.

Any animal feed blend, including those known in the art and those described herein, may be used in accordance with the methods and compositions described in this patent application, such as rapeseed meal, cottonseed meal, soybean meal, cornmeal, barley, wheat, silage, and haylage. In various embodiments, the animal feed blend can be supplemented with *Bacillus* strain 2, 3, 4, 5, 9, 57, 71, and/or 126, or strains having their identifying characteristics, and the antibiotics selected from the group consisting of ceftiofur, oxytetracycline, tulathromycin, and lincomycin, or the antibiotics can be administered separately, but other ingredients may optionally be added to the animal feed blend, including other different bacterial strains, such as other *Bacillus* strains or *Lactobacillus* strains.

In various illustrative embodiments, optional ingredients of the animal feed blend include sugars and complex carbohydrates such as both water-soluble and water-insoluble monosaccharides, disaccharides, and polysaccharides. Other optional ingredients include dried distillers grain solubles, fat (e.g., crude fat), phosphorous, sodium bicarbonate, limestone, salt, phytate, calcium, sodium, sulfur, magnesium, potassium, copper, iron, manganese, zinc, ash, fish oil, an oil derived from fish meal, raw seed (e.g., flaxseed), an antioxidant, and starch. In another embodiment, minerals may be added in the form of a mineral premix.

Optional amino acid ingredients that may be added to the animal feed blend are arginine, histidine, isoleucine, leucine, lysine, cysteine, methionine, phenylalanine, threonine, tryptophan, valine, tyrosine ethyl HCl, alanine, aspartic acid, sodium glutamate, glycine, proline, serine, cysteine ethyl HCl, and analogs, and salts thereof. Vitamins that may be optionally added are thiamine HCl, riboflavin, pyridoxine HCl, niacin, niacinamide, inositol, choline chloride, calcium pantothenate, biotin, folic acid, ascorbic acid, and vitamins A, B, K, D, E, and the like. In another embodiment, vitamins may be added in the form of a vitamin premix. In yet another embodiment, protein ingredients may be added to the animal feed blend and include protein obtained from meat meal, bone meal, or fish meal, liquid or powdered egg, fish solubles, crude protein, and the like.

In various embodiments, the antibiotic for use in the methods and compositions described herein is selected from the group consisting of antibiotic is selected from the group consisting of ceftiofur, oxytetracycline, tulathromycin, and lincomycin.

In various embodiments, the dosage of the antibiotic can be from about 0.1 mg/pound of feed to about 1000 mg/pound of feed, about 0.1 mg/pound of feed to about 900 mg/pound of feed, about 0.1 mg/pound of feed to about 800 mg/pound of feed, about 0.1 mg/pound of feed to about 700 mg/pound of feed, about 0.1 mg/pound of feed to about 600 mg/pound of feed, about 0.1 mg/pound of feed to about 500 mg/pound of feed, about 0.1 mg/pound of feed to about 400 mg/pound of feed, about 0.1 mg/pound of feed to about 300 mg/pound of feed, about 0.1 mg/pound of feed to about 200 mg/pound of feed, about 0.1 mg/pound of feed to about 100 mg/pound of feed, about 0.1 mg/pound of feed to about 90 mg/pound of feed, about 0.1 mg/pound of feed to about 80 mg/pound of feed, about 0.1 mg/pound of feed to about 70 mg/pound of feed, about 0.1 mg/pound of feed to about 60 mg/pound of feed, about 0.1 mg/pound of feed to about 50 mg/pound of feed, about 0.1 mg/pound of feed to about 40 mg/pound of feed, about 0.1 mg/pound of feed to about 30 mg/pound of feed, about 0.1 mg/pound of feed to about 20 mg/pound of feed, about 0.1 mg/pound of feed to about 10 mg/pound of feed, about 0.1 mg/pound of feed to about 9 mg/pound of feed, about 0.1 mg/pound of feed to about 8 mg/pound of feed, about 0.1 mg/pound of feed to about 7 mg/pound of feed, about 0.1 mg/pound of feed to about 6 mg/pound of feed, about 0.1 mg/pound of feed to about 5 mg/pound of feed, about 0.1 mg/pound of feed to about 4 mg/pound of feed, about 0.1 mg/pound of feed to about 3 mg/pound of feed, about 0.1 mg/pound of feed to about 2 mg/pound of feed, about 0.1 mg/pound of feed to about 1 mg/pound of feed, about 0.1 mg/pound of feed to about 0.5 mg/pound of feed, about 0.1 mg/pound of feed to about 0.3 mg/pound of feed, about 0.5 mg/pound of feed to about 1 mg/pound of feed, about 1 mg/ml to about 1000 mg/ml of drinking water, about 1 mg/ml to about 900 mg/ml of drinking water, about 1 mg/ml to about 800 mg/ml of drinking water, about 1 mg/ml to about 700 mg/ml of drinking water, about 1 mg/ml to about 600 mg/ml of drinking water, about 1 mg/ml to about 500 mg/ml of drinking water, about 1 mg/ml to about 400 mg/ml of drinking water, about 1 mg/ml to about 300 mg/ml of drinking water, about 1 mg/ml to about 200 mg/ml of drinking water, about 1 mg/ml to about 100 mg/ml of drinking water, about 50 mg/ml to about 100 mg/ml of drinking water, about 50 mg/ml to about 90 mg/ml of drinking water, about 50 mg/ml to about 80 mg/ml of drinking water, about 50 mg/ml to about 70 mg/ml of drinking water, about 50 mg/ml to about 60 mg/ml of drinking water, about 1000 ppm, about 900 ppm, about 800 ppm, about 700 ppm, about 600 ppm, about 500 ppm, about 400 ppm, about 300 ppm, about 200 ppm, about 100 ppm, about 90 ppm, about 80 ppm, about 70 ppm, about 60 ppm, about 50 ppm, about 40 ppm, about 30 ppm, about 20 ppm, or about 10 ppm.

In another illustrative embodiment, one or more enzymes may be added to the animal feed blend or to the feed composition or feed additive or the bacterial strain. In various embodiments, the enzymes that may be added include a galactosidase, a phytase, a protease, a lipase, an amylase, a hemicellulase, an arabinoxylanase, a xylanase, a cellulase, an NSPase, combinations thereof, and any other enzyme that improves the effectiveness of the feed composition or feed additive for *E. coli* inhibition or controlling a detrimental effect of *E. coli*. In yet another embodiment, yeast, fungi (e.g., *Aspergillus* or *Trichoderma*), or micronutrients may be added to the animal feed, feed composition, or feed additive, or the bacterial strain. Any of the ingredients described above that are suitable for addition to an additive for the drinking water of the animal may be added as a component of the additive for the drinking water of the animal as described herein.

In various illustrative embodiments, the *Bacillus* strain (e.g., *Bacillus* strain 2, 3, 4, 5, 9, 57, 71, and/or 126, or strains having their identifying characteristics), or any other different bacterial strains added in addition to *Bacillus* strain 2, 3, 4, 5, 9, 57, 71, and/or 126, or strains having their identifying characteristics, can be administered in the feed composition at a dose of about $1.0\times10^3$ CFU/gram of the feed composition to about $5.0\times10^{12}$ CFU/gram of the feed composition or at a dose of about $1.0\times10^3$ CFU/gram of the feed composition to about $1.0\times10^7$ CFU/gram of the feed composition. In other embodiments, the *Bacillus* strain (e.g., *Bacillus* strain 2, 3, 4, 5, 9, 57, 71, and/or 126, or strains having their identifying characteristics) is administered in the feed composition at a dose greater than about $1.0\times10^3$ CFU/gram of the feed composition, at a dose greater than about $1.1\times10^3$ CFU/gram of the feed composition, at a dose greater than about $1.25\times10^3$ CFU/gram of the feed composition, at a dose greater than about $1.5\times10^3$ CFU/gram of the feed composition, at a dose greater than about $1.75\times10^3$ CFU/gram of the feed composition, at a dose greater than about $1.0\times10^4$ CFU/gram of the feed composition, at a dose greater than about $2.0\times10^4$ CFU/gram of the feed composition, at a dose greater than about $3.0\times10^4$ CFU/gram of the feed composition, at a dose greater than about $4.0\times10^4$ CFU/gram of the feed composition, at a dose greater than about $5.0\times10^4$ CFU/gram of the feed composition, at a dose greater than about $6.0\times10^4$ CFU/gram of the feed composition, at a dose greater than about $7.0\times10^4$ CFU/gram of the feed composition, at a dose greater than about $8.0\times10^4$ CFU/gram of the feed composition, at a dose greater than about $1.0\times10^5$ CFU/gram of the feed composition, at a dose greater than about $1.0\times10^6$ CFU/gram of the feed composition, at a dose greater than about $1.0\times10^7$ CFU/gram of the feed composition, at a dose greater than about $1.0\times10^8$ CFU/gram of the feed composition, at a dose greater than about $1.0\times10^9$ CFU/gram of the feed composition, at a dose greater than about $1.0\times10^{10}$ CFU/gram of the feed composition, at a dose greater than about $1.0\times10^{11}$ CFU/gram of the feed composition, or at a dose greater than about $1.0\times10^{12}$ CFU/gram of the feed composition. In another embodiment, the *Bacillus* strain (e.g., *Bacillus* strain 2, 3, 4, 5, 9, 57, 71, and/or 126, or strains having their identifying characteristics), or any other different bacterial strains added in addition to *Bacillus* strain 2, 3, 4, 5, 9, 57, 71, and/or 126, or strains having their identifying characteristics, can be administered in the feed composition at a dose of about $1.0\times10^2$ CFU/gram of the feed composition to about $5.0\times10^{12}$ CFU/gram of the feed composition or at a dose of about $1.0\times10^2$ CFU/gram of the feed composition to about $1.0\times10^7$ CFU/gram of the feed composition, or at a dose greater than about $1.0\times10^2$ CFU/gram of the feed composition. In another embodiment, any of the dosages described herein can be in CFU/ml of drinking water in embodiments where the strains are administered in the drinking water of the animal.

In various embodiments, the *Bacillus* strain (e.g., *Bacillus* strain 2, 3, 4, 5, 9, 57, 71, and/or 126, or strains having their identifying characteristics) for use in accordance with the methods or compositions described herein can be selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof. *Bacillus* strains 2, 3, 4, and 5 were deposited on Nov. 29, 2018 at the Agricultural Research Service Culture Collection (NRRL), National Center for Agricultural Utilization Research, Agricultural Research Service, USDA, 1815 North University Street, Peoria, Illinois 61604-3999, and were given accession numbers, respectively. The deposits were made under the provisions of the Budapest Treaty on the International Recognition of the Deposit of Microorganisms for the Purposes of Patent Procedure. The NRRL strain designations are NRRL No. B-67709, NRRL No. B-67710, NRRL No., B-67711, and NRRL No. B-67712, respectively. NRRL No. B-67709, NRRL No. B-67710, NRRL No., B-67711, and NRRL No. B-67712, are equivalent to *Bacillus* strains 2, 3, 4, and 5, respectively, as referred to in the application.

*Bacillus* strains 9, 57, 71, and 126 were deposited on Oct. 10, 2019 at the Agricultural Research Service Culture Collection (NRRL), National Center for Agricultural Utilization Research, Agricultural Research Service, USDA, 1815 North University Street, Peoria, Illinois 61604-3999, and were given accession numbers B-67866, B-67870, B-67867, and B-67868, respectively. The deposits were made under the provisions of the Budapest Treaty on the International Recognition of the Deposit of Microorganisms for the Purposes of Patent Procedure. NRRL No. B-67866, NRRL No. B-67870, NRRL No., B-67867, and NRRL No. B-67868, are equivalent to *Bacillus* strains 9, 57, 71, and 126, respectively, as referred to in the application. The deposit certificates refer to the strains as MDG9, MDG57, MDG71, and MDG126, respectively.

In one aspect, any of these strains can be administered alone or in combination in the form of a feed composition (e.g., a complete feed comprising an animal feed blend) or drinking water for an animal. In one embodiment, multiple strains are administered in combination in a single composition. In another embodiment, multiple strains are administered in combination in separate compositions. In yet another embodiment, any of these strains, or combinations thereof, is administered in combination with an antibiotic selected from the group consisting of ceftiofur, oxytetracycline, tulathromycin, and lincomycin, as described herein in the same or separate compositions.

In another embodiment, one or more of the *Bacillus* strains described in the preceding paragraphs (e.g., *Bacillus* strain 2, 3, 4, 5, 9, 57, 71, and/or 126, or strains having their identifying characteristics) can be administered to the animal along with another different bacterial strain selected from the group consisting of another *Bacillus* strain, a lactic acid bacterial strain, and combinations thereof. In yet another embodiment, one or more of the *Bacillus* strains described in the preceding paragraphs (e.g., *Bacillus* strain 2, 3, 4, 5, 9, 57, 71, and/or 126, or strains having their identifying characteristics) can be administered to the animal along with any other bacterial strain effective to inhibit or control detrimental effects of *E. coli* in the animal.

As used herein "a strain having all of the identifying characteristics of" *Bacillus* strain 2, 3, 4, 5, 9, 57, 71, or 126, can be a mutant strain having all of the identifying characteristics of *Bacillus* strain 2, 3, 4, 5, 9, 57, 71, or 126 (e.g., a DNA fingerprint based on DNA analysis that corresponds to the DNA fingerprint of *Bacillus* strain 2, 3, 4, 5, 9, 57, 71, or 126, enzyme activities that correspond to *Bacillus* strain 2, 3, 4, 5, 9, 57, 71, or 126, antimicrobial activity that corresponds to *Bacillus* strain 2, 3, 4, 5, 9, 57, 71, or 126, antibiotic sensitivity and tolerance profiles that correspond to *Bacillus* strain 2, 3, 4, 5, 9, 57, 71, or 126, or combinations of these identifying characteristics). In alternate embodiments, the mutation can be a natural mutation, or a genetically engineered mutation. In another embodiment, "a strain having all of the identifying characteristics of" *Bacillus* strain 2, 3, 4, 5, 9, 57, 71, or 126, can be a strain, for example, produced by isolating one or more plasmids from *Bacillus* strain 2, 3, 4, 5, 9, 57, 71, or 126, and introducing the one or more plasmids into another bacterium, such as another *Bacillus* strain, as long as the one or more plasmids contain DNA that provides the identifying characteristics of *Bacillus* strain 2, 3, 4, 5, 9, 57, 71, or 126 (e.g., a DNA fingerprint based on DNA analysis that corresponds to the DNA fingerprint of *Bacillus* strain 2, 3, 4, 5, 9, 57, 71, or 126).

The feed composition or drinking water comprising *Bacillus* strain 2, 3, 4, 5, 9, 57, 71, or 126, or strains with their identifying characteristics, and the antibiotics described herein, may be administered to the animal for any time period that is effective to inhibit *E. coli* or control a detrimental effect of *E. coli*, or combinations thereof. For example, in one embodiment the feed composition or drinking water may be provided to the animal daily. In an alternate embodiment, the feed composition or drinking water may be administered to the animal during lactation and/or during gestation. The time periods for administration of the feed composition or drinking water described above are non-limiting examples and it should be appreciated that any time period or administration schedule determined to be effective to inhibit *E. coli* or control a detrimental effect of *E. coli*, or combinations thereof, may be used.

In embodiments involving "controlling a detrimental effect of *E. coli*" controlling a detrimental effect can mean reducing *E. coli* disease, preventing *E. coli* disease, maintaining the normal microbial balance in the animal, reducing the number of detrimental *E. coli* in the animal, reducing the activity of *E. coli* in the animal, or reducing the symptoms of *E. coli* disease in the animal, or combinations thereof. By "effective amount" is meant an amount of the *Bacillus* strain (e.g., *Bacillus* strain 2, 3, 4, 5, 9, 57, 71, and/or 126) capable of controlling a detrimental effect of *E. coli* as described herein, by any mechanism.

In one embodiment, the feed additive for addition to an animal feed blend to produce a complete feed composition can be mixed with the animal feed blend, for example, with an automated micro-nutrient delivery system, or, for example, by hand-weighing and addition to achieve any of the doses of *Bacillus* strain 2, 3, 4, 5, 9, 57, 71, and/or 126, or strains with their identifying characteristics, described herein, for administration to the animal in the form of a complete feed composition. The mixing can also be done by any other suitable method known in the art for combining direct-fed microbials with an animal feed blend to obtain a uniform mixture. In various embodiments, the mixing can be done for any suitable time period (e.g., about 1 to about 4 minutes). In the embodiment where *Bacillus* strain 2, 3, 4, 5, 9, 57, 71, and/or 126, or strains with their identifying characteristics, are in the form of an additive for the drinking water of the animal, the *Bacillus* strain 2, 3, 4, 5, 9, 57, 71, and/or 126, or strains with their identifying characteristics, can be in the form of, for example, a powder, a liquid, or pellets, and can be mixed with the drinking water using any suitable method known in the art to achieve any of the doses of *Bacillus* strain 2, 3, 4, 5, 9, 57, 71, and/or 126, or strains with their identifying characteristics, described herein, for administration to the animal in the drinking water of the animal. *Bacillus* strain 2, 3, 4, 5, 9, 57, 71, and/or 126, or strains with their identifying characteristics, can also be fed directly to the animal orally (i.e., by oral insertion) in the form of a powder, a freeze-dried composition, a gel, a top-dressing, a liquid, a capsule, a paste, a liquid drench, or a pellet. Any of these embodiments can also be applied to mixing and administration of the antibiotics selected from the group consisting of ceftiofur, oxytetracycline, tulathromycin, and lincomycin described herein.

In additional embodiments of the invention, compositions are provided comprising *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

In one embodiment, a commercial package is provided comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

In another embodiment, a feed additive for an animal feed is provided comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

In yet another embodiment, an additive for the drinking water of an animal is provided comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

In yet another illustrative aspect of the invention, an animal feed composition is provided comprising an isolated *Bacillus* strain selected from the group consisting of *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof.

In one illustrative aspect, the strains for addition to the commercial package, feed additive, additive for the drinking water of the animal, or the feed composition can be in the form of a concentrate (e.g., about $1 \times 10^8$ to about $5 \times 10^9$ CFU/g) or a superconcentrate (e.g., about $1 \times 10^{10}$ to about $5 \times 10^{12}$ CFU/g). In another embodiment, the strains for addition to the commercial package, feed additive, feed composition, or additive for the drinking water of the animal can be in a dry form (e.g., a powder), a pelleted form, a liquid form, a liquid drench, a powder, a freeze-dried composition, in the form of a top-dressing, a paste, or in the form of a gel, or any other suitable form.

In another illustrative embodiment, the strain or strains in the commercial package, the feed additive, additive for the drinking water of the animal, or feed composition can further comprise a carrier for the *Bacillus* strain or strains. The carrier can be selected from the group consisting of a bran, rice hulls, a salt, mineral oil, a dextrin (e.g., malto-dextrin), whey, sugar, sucrose, limestone, yeast culture, dried starch, sodium silico aluminate, silicon dioxide, poly-propylene glycol, polysorbate 80, vegetable oil, and combinations thereof. In another embodiment, the carrier can be any suitable carrier known in the art for a direct-fed micro-bial. The carrier is exogenously added to the bacterial strain (i.e., not naturally present or not present in nature with the bacterial strain). In another embodiment, the feed additive, additive for the drinking water of the animal, or feed composition can further comprise a binder such as clay, yeast cell wall components, aluminum silicate, glucan, or other known binders. In another embodiment, the commercial package, feed additive, additive for the drinking water of the animal, or feed composition can further comprise inorganic/organic binders, essential oils, and/or organic acids. The binder is exogenously added to the bacterial strain (i.e., not naturally present or not present in nature with the bacterial strain).

In yet other embodiments, the commercial package, feed additive, additive for the drinking water of the animal, or feed composition comprising *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No.

B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, is in a container for commercial use.

In various embodiments the container can be, for example, a bag (e.g., a 20-pound bag, a 50-pound bag, a 2-ounce bag, a 1-pound bag, or a 1-kilogram bag), a pouch, a drum, a bottle, or a box. In illustrative aspects, the container for the commercial package, feed additive, additive for the drinking water of the animal, or feed composition comprising *Bacillus* strain 2 (NRRL No. B-67709), a strain having all of the identifying characteristics of *Bacillus* strain 2 (NRRL No. B-67709), *Bacillus* strain 3 (NRRL No. B-67710), a strain having all of the identifying characteristics of *Bacillus* strain 3 (NRRL No. B-67710), *Bacillus* strain 4 (NRRL No. B-67711), a strain having all of the identifying characteristics of *Bacillus* strain 4 (NRRL No. B-67711), *Bacillus* strain 5 (NRRL No. B-67712), a strain having all of the identifying characteristics of *Bacillus* strain 5 (NRRL No. B-67712), *Bacillus* strain 9 (NRRL No. B-67866), a strain having all of the identifying characteristics of *Bacillus* strain 9 (NRRL No. B-67866), *Bacillus* strain 57 (NRRL No. B-67870), a strain having all of the identifying characteristics of *Bacillus* strain 57 (NRRL No. B-67870), *Bacillus* strain 71 (NRRL No. B-67867), a strain having all of the identifying characteristics of *Bacillus* strain 71 (NRRL No. B-67867), *Bacillus* strain 126 (NRRL No. B-67868), a strain having all of the identifying characteristics of *Bacillus* strain 126 (NRRL No. B-67868), and combinations thereof, can comprise plastic, metal, foil, paper, fiber, or cardboard (e.g., a plastic pail, a paper bag, a foil bag, a fiber drum, etc.). The commercial package, feed additive, additive for the drinking water of the animal, or feed composition can further comprise instructions for use of one or more of the *Bacillus* strains.

In one aspect, the commercial package, feed additive, additive for the drinking water of the animal, or feed composition described herein can further comprise an exogenously added nutrient component (i.e., a nutrient component not present with the bacterial strain in nature) selected from the group consisting of a vitamin, an antibiotic, an enzyme, a water-soluble or water-insoluble monosaccharide, disaccharide, or polysaccharide, a fat, phosphorous, sodium bicarbonate, limestone, calcium, sodium, sulfur, magnesium, potassium, copper, iron, manganese, zinc, fish oil, raw seed, an antioxidant, and a starch.

In one embodiment, the exogenously added nutrient component is an enzyme and the enzyme is selected from the group consisting of a galactosidase, a protease, a lipase, an amylase, a hemicellulase, an arabinoxylanase, a xylanase, a cellulase, an NSPase, a phytase, and combinations thereof.

In one embodiment, any of the compositions described herein can be a dietary nutrient composition (e.g., a probiotic composition).

In some embodiments of the methods and compositions described herein, synergism occurs between the *Bacillus* strains and the antibiotics.

The following examples are for illustrative purposes only. The examples are non-limiting, and are not intended to limit the invention in any way.

EXAMPLE 1

*Bacillus* Testing on Excede (12), Draxxin (8), Lincomix (12), and Liquamycin (11) resistant *E. Coli*

Utilizing a broth AST method, four *Bacillus* strains were tested against 12 Excede-resistant *E. coli,* 8 Draxxin-resistant *E. coli,* 12 Linocmix-resistant *E. coli,* and 11 Liquamycin-resistant *E. coli.* An additional four *Bacillus* strains were identified and tested in identical fashion against the same Lincomycin-resistant *E. coli.*

*Bacillus* strain 2 (NRRL No. B-67709), *Bacillus* strain 3 (NRRL No. B-67710), *Bacillus* strain 4 (NRRL No. B-67711), *Bacillus* strain 5 (NRRL No. B-67712), *Bacillus* strain 9 (NRRL No. B-67866), *Bacillus* strain 57 (NRRL No. B-67870), *Bacillus* strain 71 (NRRL No. B-67867), and *Bacillus* strain 126 (NRRL No. B-67868), consistently improved and effectively inhibited (>50% inhibition) antibiotic resistant pathogens when the same concentration of antibiotic was administered in conjunction with *Bacillus* supernatant.

Of the 12 Excede-resistant *E. coli*: when combined with antibiotics *Bacillus* strains 9, 57, and 71 effectively inhibited 11/12 isolates. When combined with antibiotics *Bacillus* strain 126 effectively inhibited 10/12 isolates.

Of the 12 Liquamycin resistant *E. coli*: when combined with antibiotics *Bacillus* strains 9, 57, 71, and 126 improved inhibition in 12/12 isolates.

Of the 8 Draxxin resistant *E. coli*: when combined with antibiotics *Bacillus* strains 9, 57, 71, and 126 improved inhibition in 8/8 isolates.

Of the 12 Lincomix resistant *E. coli*: when combined with antibiotics *Bacillus* strain 9 improved inhibition in 11/12 isolates. When combined with antibiotics *Bacillus* strains 57, 71, and 96 improved inhibition in 12/12 isolates. When compared to Lincomix alone, *Bacillus* strains 9, 57, 71, and 126 superiorly inhibited 12/12 isolates. When compared to Lincomix alone, *Bacillus* strains 2, 3, 4, and 5 superiorly inhibited 11/12 isolates.

The goal of this project was to identify *Bacillus* strains that exhibit strong inhibition potential of target pathogens in combination with antibiotics. This synergy can be defined as a resulting higher percent inhibition of antibiotic-resistant pathogens when *Bacillus* supernatants are combined with antibiotics than when the supernatant and antibiotic are tested separately against the same isolates. Eight *Bacillus* strains yielded consistent strong inhibition activity against Excede, Draxxin, Lincomix, and Liquamycin-resistant *E. coli* tested.

EXAMPLE 2

RAPD-PCR DNA Profiles

Figure 6:
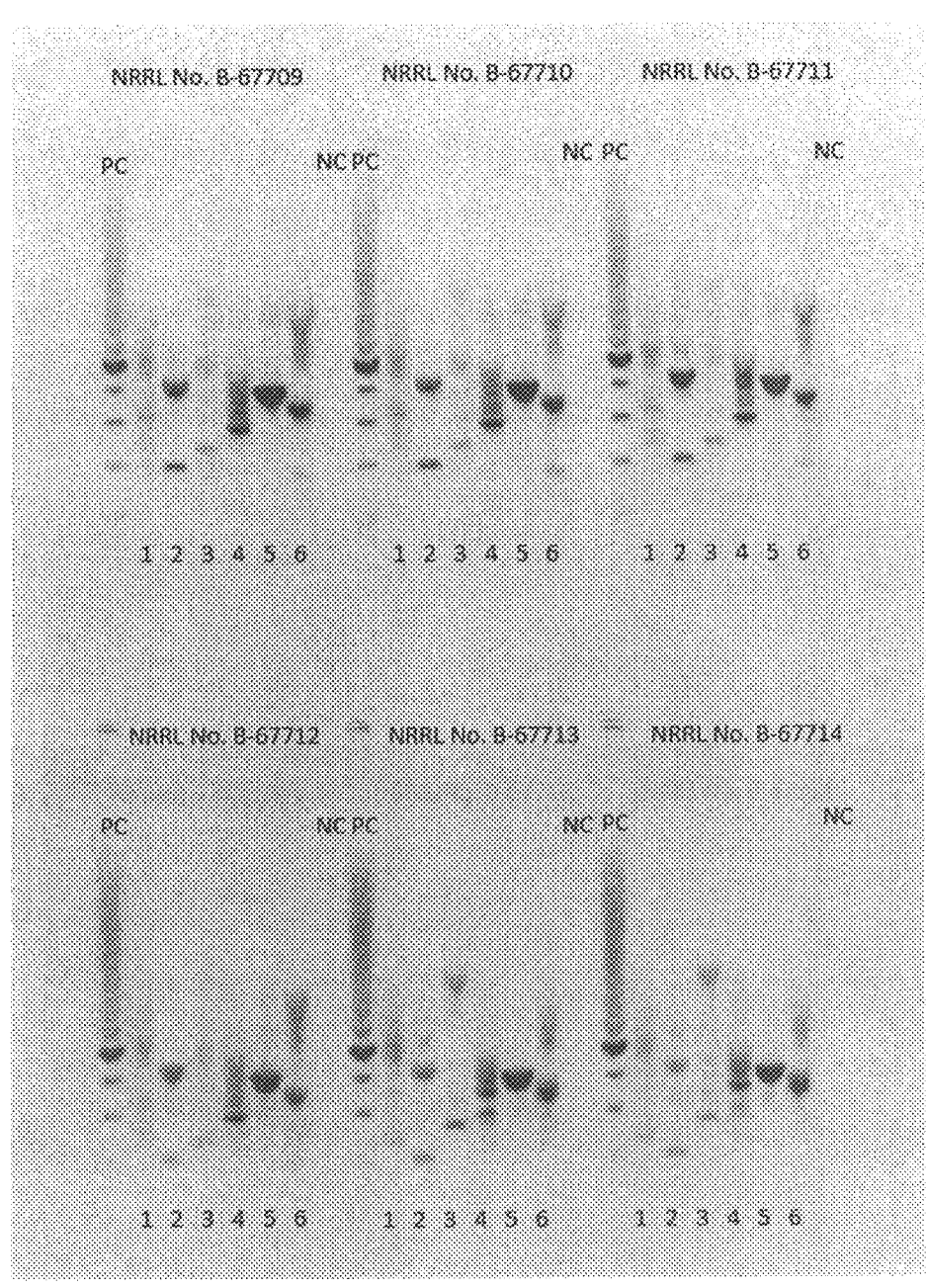
FIG. 6 is a photograph displaying RAPD PCR profiles for *Bacillus* strain 2 (NRRL No. B-67709), *Bacillus* strain 3 (NRRL No. B-67710), *Bacillus* strain 4 (NRRL No. B-67711), *Bacillus* strain 5 (NRRL No. B-67712), *Bacillus* strain 6 (NRRL No. B-67714), and *Bacillus* strain 7 (NRRL No. B-67713).
Figure 7:
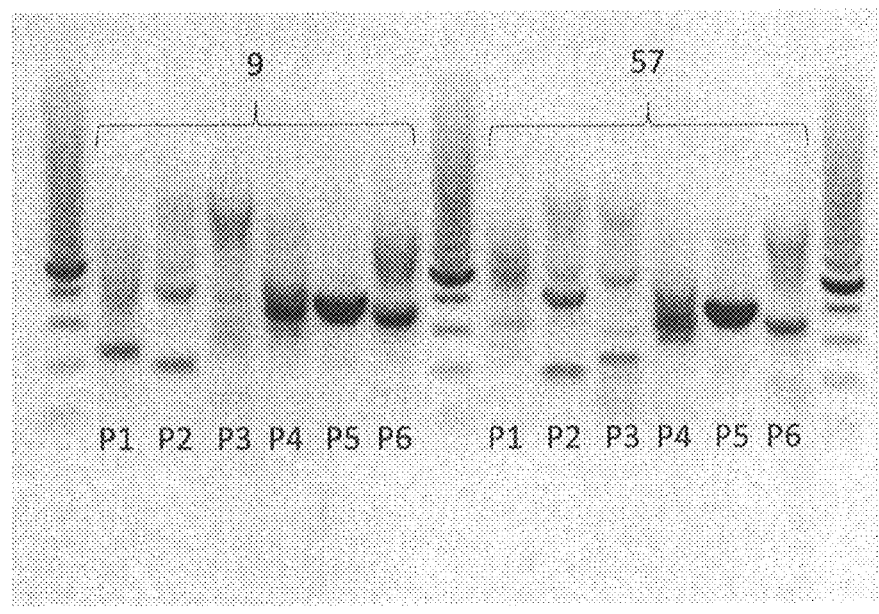
FIG. 7 is a photograph displaying RAPD PCR profiles for *Bacillus* strain 9 (NRRL No. B-67866) and *Bacillus* strain 57 (NRRL No. B-67870).
Figure 8:
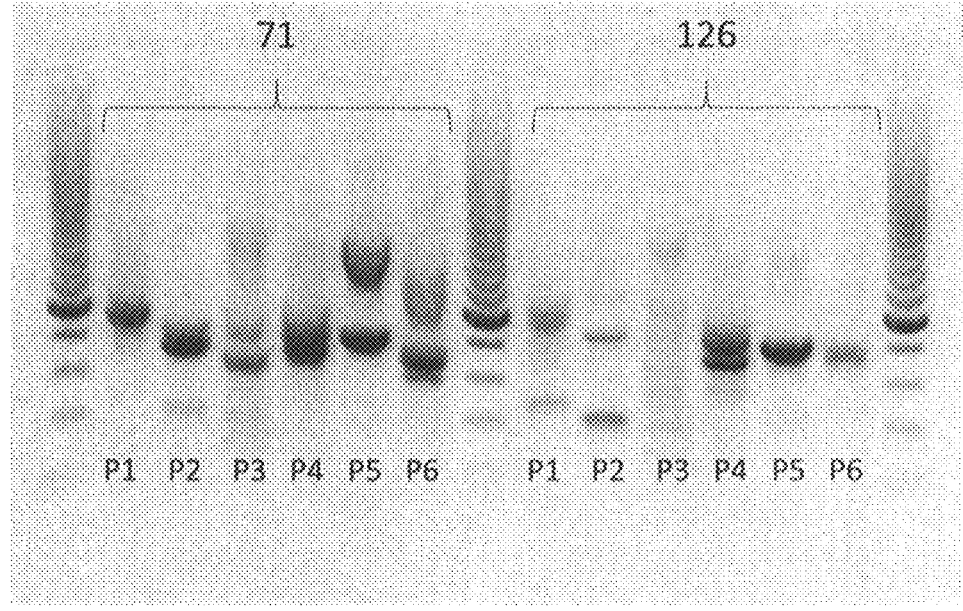
FIG. 8 is a photograph displaying RAPD PCR profiles for *Bacillus* strain 71 (NRRL No. B-67867) and *Bacillus* strain 126 (NRRL No. B-67868).

The Randomly Amplified Polymorphic DNA PCR method (hereafter referred to as RAPD-PCR) was used to identify genetic variability of each strain. Preparation of the DNA to be used in the RAPD-PCR reaction was done by using the QIAGEN® Tissue and Blood single column kit (QIAGEN®, Venlo, The Netherlands). FIGS. 6, 7, and 8 illustrate RAPD-PCR results for strains 2, 3, 4, 5, 6, 7, 9, 57, 71, and 126, with the unlabeled lanes or the lanes labeled "PC" being a molecular weight ladder. The results show that all strains are unique from each other.

What is claimed is:

1. A method of feeding an animal, the method comprising the step of administering to the animal a feed composition or drinking water comprising an effective amount of an additive comprising an isolated *Bacillus* strain selected from the group consisting of *Bacillus* strain 2 (NRRL No. B-67709), *Bacillus* strain 3 (NRRL No. B-67710), *Bacillus* strain 4 (NRRL No. B-67711), *Bacillus* strain 5 (NRRL No. B-67712), *Bacillus* strain 9 (NRRL No. B-67866), *Bacillus* strain 57 (NRRL No. B-67870), *Bacillus* strain 71 (NRRL No. B-67867), *Bacillus* strain 126 (NRRL No. B-67868), and combinations thereof, and administering to the animal an antibiotic wherein the antibiotic is selected from the group consisting of ceftiofur, oxytetracycline, tulathromycin, and lincomycin.

2. The method of claim 1 wherein the animal is selected from the group consisting of a poultry species, a porcine species, a caprine species, a bovine species, an ovine species, an equine species, and a companion animal.

3. The method of claim 1 wherein the animal is a porcine species and the porcine species is selected from the group consisting of a grow finish pig, a nursery pig, a sow, and a breeding stock pig.

4. The method of claim 1 wherein the *Bacillus* strain produces an enzyme selected from the group consisting of an α-galactosidase, a protease, a lipase, an amylase, a xylanase, a cellulase, and combinations thereof.

5. The method of claim 1 further comprising the step of administering to the animal another different bacterial strain selected from the group consisting of another *Bacillus* strain, a lactic acid bacterial strain, and combinations thereof.

6. The method of claim 1 wherein the strain administered is *Bacillus* strain 2 (NRRL No. B-67709) in combination with one or more *Bacillus* strains selected from *Bacillus* strain 9 (NRRL No. B-67866), *Bacillus* strain 57 (NRRL No. B-67870), *Bacillus* strain 71 (NRRL No. B-67867) and *Bacillus* strain 126 (NRRL No. B-67868).

7. The method of claim 1 wherein the strain administered is *Bacillus* strain 3 (NRRL No. B-67710) in combination with one or more *Bacillus* strains selected from *Bacillus* strain 9 (NRRL No. B-67866), *Bacillus* strain 57 (NRRL No. B-67870), *Bacillus* strain 71 (NRRL No. B-67867) and *Bacillus* strain 126 (NRRL No. B-67868).

8. The method of claim 1 wherein the strain administered is *Bacillus* strain 4 (NRRL No. B-67711) in combination with one or more *Bacillus* strains selected from *Bacillus* strain 9 (NRRL No. B-67866), *Bacillus* strain 57 (NRRL No. B-67870), *Bacillus* strain 71 (NRRL No. B-67867) and *Bacillus* strain 126 (NRRL No. B-67868).

9. The method of claim 1 wherein the strain administered is *Bacillus* strain 5 (NRRL No. B-67712) in combination with one or more *Bacillus* strains selected from *Bacillus* strain 9 (NRRL No. B-67866), *Bacillus* strain 57 (NRRL No. B-67870), *Bacillus* strain 71 (NRRL No. B-67867) and *Bacillus* strain 126 (NRRL No. B-67868).

10. The method of claim 1 wherein the *Bacillus* strain is administered in the feed composition at a dose of about $1.0 \times 10^3$ CFU/gram of the feed composition to about $5.0 \times 10^{12}$ CFU/gram of the feed composition.

11. The method of claim 1 wherein the *Bacillus* strain is administered in the feed composition at a dose of about $1.0 \times 10^3$ CFU/gram of the feed composition to about $1.0 \times 10^7$ CFU/gram of the feed composition.

12. The method of claim 1 wherein the *Bacillus* strain is administered in the feed composition at a dose greater than about $7.0 \times 10^4$ CFU/gram of the feed composition.

13. The method of claim 1 further comprising the step of administering to the animal an enzyme selected from the group consisting of a galactosidase, a protease, a lipase, an amylase, a hemicellulase, an arabinoxylanase, a xylanase, a cellulase, an NSPase, a phytase, and combinations thereof.

14. The method of claim 1 wherein the animal is a sow and the *Bacillus* strain is administered during lactation.

15. The method of claim 1 wherein the animal is a sow and the *Bacillus* strain is administered during gestation.

16. The method of claim 1 wherein the feed composition is administered daily to the animal.

17. The method of claim 1 wherein the animal is selected from the group consisting of a chicken, a pig, a horse, a pony, a cow, a turkey, a goat, a sheep, a quail, a pheasant, an ostrich, a duck, a fish, a crustacean, and combinations thereof.

18. The method of claim 1 wherein the *Bacillus* strain has an effect selected from the group consisting of maintaining microbial balance in the gut of the animal, improving animal performance or health, maintaining gut health in the animal, reducing detrimental pathogens in the gut of the animal, odor reduction, reducing detrimental pathogens in the urine or feces of the animal, and preserving the growth of beneficial bacteria in the gut of the animal.

19. The method of claim 1 wherein the strain administered is *Bacillus* strain 9 (NRRL No. B-67866).

20. The method of claim 1 wherein the strain administered is *Bacillus* strain 57 (NRRL No. B-67870).

21. The method of claim 1 wherein the strain administered is *Bacillus* strain 71 (NRRL No. B-67867).

22. The method of claim 1 wherein the strain administered is *Bacillus* strain 126 (NRRL No. B-67868) in combination with one or more *Bacillus* strains selected from *Bacillus* strain 9 (NRRL No. B-67866), *Bacillus* strain 57 (NRRL No. B-67870), *Bacillus* strain 71 (NRRL No. B-67867), *Bacillus* strain 2 (NRRL No. B-67709), *Bacillus* strain 3 (NRRL No. B-67710), *Bacillus* strain 4 (NRRL No. B-67711) and *Bacillus* strain 5 (NRRL No. B-67712).

* * * * *